US008997998B2

(12) United States Patent
Curran et al.

(10) Patent No.: US 8,997,998 B2
(45) Date of Patent: Apr. 7, 2015

(54) CONTROLLER FOR AN ACOUSTIC STANDING WAVE GENERATION DEVICE IN ORDER TO PREVENT CLOGGING OF A FILTER

(75) Inventors: Stephen John Curran, Heslington (GB); Jonathan Nicholas Ridgway, Heslington (GB); Pei-Sheng Chen, Heslington (GB); Michael Pratt, London (GB); Marc Tanner, London (GB); Stephen Latham, Sun Prairie, WI (US); Nick Reback, Madison, WI (US)

(73) Assignee: Smith & Nephew PLC, London (GB)

( * ) Notice: Subject to any disclaimer, the term of this patent is extended or adjusted under 35 U.S.C. 154(b) by 1082 days.

(21) Appl. No.: 13/054,993

(22) PCT Filed: Jul. 24, 2009

(86) PCT No.: PCT/GB2009/001830
§ 371 (c)(1),
(2), (4) Date: Sep. 15, 2011

(87) PCT Pub. No.: WO2010/010355
PCT Pub. Date: Jan. 28, 2010

(65) Prior Publication Data
US 2011/0315641 A1  Dec. 29, 2011

(30) Foreign Application Priority Data

Jul. 25, 2008 (GB) .................................. 0813644.2
Sep. 24, 2008 (GB) .................................. 0817515.0

(51) Int. Cl.
*C02F 1/36* (2006.01)
*G01N 1/40* (2006.01)

(52) U.S. Cl.
CPC ................................. *G01N 1/4077* (2013.01)

(58) Field of Classification Search
CPC ........... C02F 1/34; C02F 1/36; B01D 29/865; G01N 1/34; C12M 3/06
USPC ................................. 210/384, 748.02, 748.05
See application file for complete search history.

(56) References Cited

U.S. PATENT DOCUMENTS 5,085,783 A    2/1992  Feke et al.
5,472,605 A   12/1995  Zuk (Continued)

FOREIGN PATENT DOCUMENTS

DE         20119909 U1    8/2002
EP          1055445 A2   11/2000

(Continued)

OTHER PUBLICATIONS

English Translation and Second Office Action for Chinese Patent Application No. 20090129165.6 dated Dec. 5, 2013, 8 pages.

(Continued)

*Primary Examiner* — Fred Prince
(74) *Attorney, Agent, or Firm* — David L. Fox; JL Salazar Law Firm

(57) ABSTRACT

The invention relates to a method and apparatus to continuously monitor and control acoustic energy and vacuum pressure to maintain a net unidirectional flow of multi-phase heterogeneous fluids through a porous filter or membrane. The heterogenous fluid may come form a variety of sources including biological sources such as, blood, bone marrow aspirate (BMA), adipose tissue (lipoaspirate), urine, saliva, etc.

14 Claims, 28 Drawing Sheets

(56) References Cited

U.S. PATENT DOCUMENTS

| | | | |
|---|---|---|---|
| 5,724,988 A | 3/1998 | Dennehey et al. | |
| 5,915,161 A * | 6/1999 | Adams | 422/186.3 |
| 5,948,441 A | 9/1999 | Lenk et al. | |
| 6,139,757 A | 10/2000 | Ohmura et al. | |
| 6,213,311 B1 | 4/2001 | Coric | |
| 6,221,258 B1 | 4/2001 | Feke et al. | |
| 6,268,119 B1 | 7/2001 | Sumita et al. | |
| 6,406,622 B1 | 6/2002 | Tsuihiji et al. | |
| 6,428,709 B1 | 8/2002 | Tsuihiji et al. | |
| 6,461,524 B1 | 10/2002 | Tsuihiji et al. | |
| 6,543,455 B2 | 4/2003 | Bonutti | |
| 6,797,158 B2 | 9/2004 | Feke et al. | |
| 6,878,371 B2 | 4/2005 | Ueno et al. | |
| 7,166,443 B2 | 1/2007 | Walker et al. | |
| 7,291,450 B2 | 11/2007 | Sowemimo et al. | |
| 7,316,932 B2 | 1/2008 | Woodside | |
| 7,364,657 B2 | 4/2008 | Mandrusov et al. | |
| 2002/0039786 A1 | 4/2002 | Reid et al. | |
| 2002/0182186 A1 | 12/2002 | Loeb | |
| 2003/0084929 A1 | 5/2003 | Kamikawa et al. | |
| 2004/0152190 A1 | 8/2004 | Sumita | |
| 2005/0147597 A1 | 7/2005 | Ueno et al. | |
| 2005/0189297 A1 | 9/2005 | Bosch et al. | |
| 2005/0205498 A1 | 9/2005 | Sowemimo et al. | |
| 2006/0251628 A1 | 11/2006 | Attawia et al. | |
| 2007/0275459 A1 | 11/2007 | Terashima et al. | |
| 2008/0014181 A1 | 1/2008 | Ariff et al. | |
| 2008/0081033 A1 | 4/2008 | Sowemimo-Coker et al. | |
| 2008/0081367 A1 | 4/2008 | Sowemimo-Coker et al. | |
| 2008/0108047 A1 | 5/2008 | Woodside | |
| 2008/0145345 A1 | 6/2008 | Mandrusov et al. | |

FOREIGN PATENT DOCUMENTS

| | | |
|---|---|---|
| EP | 1055447 A2 | 11/2000 |
| EP | 1055448 A2 | 11/2000 |
| EP | 1252293 A1 | 10/2002 |
| EP | 1303588 A2 | 4/2003 |
| EP | 1484390 A1 | 12/2004 |
| EP | 1683857 A1 | 7/2006 |
| EP | 1728857 A3 | 4/2007 |
| GB | 2235882 | 3/1991 |
| GB | 2235882 A | 3/1991 |
| GB | 2430393 A | 3/2007 |
| JP | 9121849 A | 5/1997 |
| JP | 9121850 A | 5/1997 |
| JP | 9322758 A | 12/1997 |
| JP | 2001-070762 | 3/2001 |
| JP | 2004-258614 | 9/2004 |
| WO | 94/21361 A | 9/1994 |
| WO | 00/074814 | 12/2000 |
| WO | WO0134167 A1 | 5/2001 |
| WO | WO2006014156 A1 | 2/2006 |
| WO | WO2006014158 A1 | 2/2006 |
| WO | WO2006128100 A2 | 11/2006 |
| WO | WO2007/034521 A1 | 3/2007 |
| WO | WO2007139551 A1 | 12/2007 |

OTHER PUBLICATIONS

English Translation and Notice of Reasons for Rejection for Japanese Patent Application No. 2011-519236 dated Jan. 7, 2014, 7 pages.

English Translation and First Office Action for Chinese Patent Application No. 200980129165.6 dated Mar. 19, 2013, 5 pages.

Groschl, M, "Ultrasonic Separation of Suspended Particles—Part I: Fundamentals", CPME1045651P, Acustica, vol. 84, 1998, pp. 442-447.

English Translation of Office Action for Chinese Patent Application No. 200980129165.6 dated Mar. 19, 2013, 5 pages.

International Preliminary Report for Patentability for PCT Patent Application No. PCT/GB209/001830 dated Jan. 25, 2011, 12 pages.

Groschl, M. Ultrasonic Spearation of Suspended Particles- Part I: Fundamentals, vol. 84 (1998), 16 pages.

International Search Report in PCT/GB2009/001830, mailed Jun. 21, 2010, 6 pages.

Examination Report for Australian Patent Application No. 2009275287 dated Jul. 3, 2014, 3 pages.

Third Office Action and Translation for Chinese Patent Application No. 200980129165.6 dated Jun. 20, 2014, 6 pages.

* cited by examiner

Θ  =Tilt angle
O  =Length of relaxed spring - compressed spring
A  =Distance between the hinge and the spring

CONTROLLER FOR AN ACOUSTIC STANDING WAVE GENERATION DEVICE IN ORDER TO PREVENT CLOGGING OF A FILTER

RELATED APPLICATIONS

The present application relates to an invention that improves upon and can be used with a separation apparatus as disclosed in UK provisional application no. 0704180.9 filed on 2 Mar. 2007, UK provisional application no. 0722448.8 filed on 15 Nov. 2007, UK provisional application no. 0801901.0 filed on 1 Feb. 2008 and International patent application no. PCT/GB2008/000704 filed on 29 Feb. 2008, all of which are herein incorporated in their entirety.

FIELD OF THE INVENTION

The invention relates to a method and apparatus to continuously monitor and control acoustic energy and vacuum pressure to maintain a net unidirectional flow of multi-phase heterogeneous fluids through a porous filter or membrane. The heterogeneous fluid may come form a variety of sources including biological sources such as, blood, bone marrow aspirate (BMA), adipose tissue (lipoaspirate), urine, saliva, etc.

Particular embodiments of the present invention further relate to an apparatus and/or system for efficient and aseptic retrieval of a thin film of a biological fluid.

BACKGROUND TO THE INVENTION

It is known from International patent application no. PCT/GB2008/000704 to provide a separation apparatus adapted to maintain a unidirectional flow across a porous filter using a vacuum pump and acoustic standing waves that keep the pores of the filter clear. It has been found by the present Applicant that as the fluid volume retained above the filter reduces, the frequency and amplitude of the acoustics also need to change to prevent blockage of the filter.

U.S. Pat. No. 5,997,490 discloses a system for applying energy to the human body in order to treat bone fractures and osteoporosis by effecting high frequency, low stress stimulation to a fracture or treatment site. The applied energy is such as to cause cyclical displacement or cyclical forces to the bone. There is provided a feedback and control system to apply the energy according to a formula.

US 2007/0249046 discloses a device for ultrasonic treatment, of tissue injuries and to augment the maturation and differentiation of stem cell populations. The device optionally includes a controller with a timer and a display.

BRIEF SUMMARY OF THE DISCLOSURE

According to a first aspect of the invention there is provided apparatus for separating a solid fraction from a fluid sample, the apparatus comprising a filtration unit, the filtration unit comprising;

an acoustic energy generating element;
at least one filter which divides the unit into a pre-filtration chamber for receiving the fluid sample and a post-filtration chamber for receiving a fluid capable of transmitting acoustic waves; and
a substrate configured to be associated with post-filtration chamber, the substrate being capable of resonation upon application of acoustic'energy thereto;
wherein the acoustic energy generating element is configured to be associated with the substrate such that the acoustic energy generating element is operable to cause resonation of the substrate which in turn transmits an acoustic standing wave through both the fluid within the post-filtration chamber and the fluid sample within the pre-filtration chamber;
wherein the apparatus further comprises weight sensing means to measure a weight of fluid in the pre-filtration chamber; and
wherein the apparatus further comprises a controller adapted to control at least the acoustic energy generating element so as to adjust characteristics of the acoustic standing wave as a function of the measured weight of fluid in the pre-filtration chamber.

It will be understood that the measured weight of fluid in the pre-filtration chamber can be used as a measure of a volume of fluid in the pre-filtration chamber on one side of the filter, since a density of the fluid will be known or can be determined.

The weight sensing means in a preferred embodiment may comprise, a load cell, preferably a calibrated load cell, located underneath the post-filtration chamber, for example underneath the acoustic energy generating element.

Advantageously, the apparatus further comprises suction means to remove fluid from the post-filtration chamber, thereby applying a vacuum pressure across the filter so as to generate a net unidirectional flow of biological fluids (multi-phase heterogeneous fluids) through the filter from the pre-filtration chamber to the post-filtration chamber.

Where suction means is provided, there is preferably also provided a pressure sensor to measure the vacuum pressure. The pressure sensor is advantageously linked to the controller, and the controller to the suction means, thereby to provide feedback-based control of the vacuum pressure.

The apparatus may additionally include a monitor for measuring acoustic energy delivered to the fluid, for example a microphone or other acoustic sensing device. The monitor is advantageously linked to the controller, and the controller to the acoustic energy generating element, thereby to provide feedback-based control of the acoustic standing wave, for example to control wavelength, frequency, amplitude, intensity and/or energy of the acoustic standing wave.

The controller may be provided with or linked to a display, for example a liquid crystal or light emitting diode display, which can be arranged to display fluid weight and/or volume, vacuum pressure and/or acoustic wave characteristics.

In particularly preferred embodiments, the controller and at least one of the display, the suction means, the pressure sensor and the acoustic energy monitor are integrated on a printed circuit board (PCB) that also includes a microprocessor.

Advantageously, changes in fluid volume, pressure and/or acoustic energy are registered by the microprocessor which intelligently adjusts the acoustic energy generating element and the suction means to deliver preferred levels of acoustic energy and pressure to process the biological fluid through the separation device.

Net unidirectional flow of the biological fluid through the filter may be achieved, by mechanical suction using the suction means, which may comprise a vacuum pump. Appropriate vacuum pressure is applied and maintained to allow movement of desired components of the biological fluid through the filter whilst retaining the biological integrity, functionality and viability of the cells in the fluid sample.

Appropriate acoustic energy (frequency and amplitude) is applied to the biological fluid by the acoustic energy generating element to create filter vibration and/or agitation of the cells in the fluid sample. This minimises or at least reduces a contact time between the cells on the filter surface and prevents the pores on the filter becoming occluded with larger cells or particles in the fluid. As the fluid volume above the filter reduces, the acoustic energy that is delivered into the fluid can be changed to keep the pores clear.

In addition to varying the applied process parameters as described above, the controller of embodiments of the present invention may also be configured to terminate the separation process upon detection of predetermined events, such as the filter being blocked or clogged, the volume of pre-filtration fluid reaching zero, an unexpected loss of vacuum pressure (indicating a leak in the system), for example.

The transmission of an acoustic standing wave through the fluids within the filtration unit results in the agitation of the fluids, either continuously or in a pulsed manner, during the separation process. A particular advantage of this agitation is that it reduces fouling and clogging of the filter.

In embodiments of the invention in which the apparatus is being utilised to separate a cellular fraction from a fluid sample, the agitation of the fluids in the unit has a further advantage in that it minimises the contact time or residence time of the cells within the pre-filtration chamber with the filter. This is desirable because if the cells are in contact with or sufficiently adjacent to the surface of the filter there is tendency for the cells to be forced through pores under the pressure of the surrounding fluid. Such passage through the pore is achievable by the deformation of the cell, but during the passage the cells may be exposed to undesirable stresses, such as shear stress, which may have deleterious effects on the cell. In particular it has been shown that white cell function can be significantly affected by shear stresses (Carter et al, 2003). It is therefore desirable to prevent the cells of interest from passing through the filter. In this regard the filter is designed to allow the passage of fluid and other cellular fractions whilst retaining the cells of interest in the pre-filtration chamber.

An acoustic energy generating element is defined as a structure that can generate an acoustic energy field in response to a power signal. For example, in the case of a simple speaker, the power signal will physically deflect a diaphragm at a defined amplitude and frequency to generate the acoustic wave. Other acoustic elements include piezoelectric transducers that generate vibrational energy in response to applied AC voltages and the physical vibration is transferred to the fluid as an acoustic force. Examples of piezoelectric elements are ceramic substrates, for example thin discs or other shapes, with metals film electrodes on each side, these thin piezoelectric films are typically zinc-oxide.

The association of an acoustic energy generating element with a substrate capable of resonation has a number of advantages over the use of an acoustic element alone. The acoustic element is not in direct contact with the fluid as this element is designed to provide improved resonance when attached to a substrate material which has a much larger area than the cone of the element itself. This means more energy can be delivered to the fluid whilst still using a small acoustic element. Overall this significantly improves energy efficiency and footprint of the device, which is particularly advantageous when processing large fluid volumes. A suitable acoustic element can be obtained from NXT Technology Limited (Hong Kong), Model No. RM-ETN0033K19C-2K01.

In embodiments of the invention the acoustic energy generating element in combination with a substrate generates an acoustic standing wave having a frequency in the range of between about 300-700 Hz. A relationship exists between the fluid volume and the optimal frequency required. Therefore, advantageously in particular embodiments of the invention the user can input the volume of the fluid sample and the frequency of the acoustic standing wave will be calculated. For example, for a sample having a volume of between about 5 ml to 15 ml, the optimal frequency of the acoustic standing wave is between about 300 Hz to 700 Hz.

In a specific embodiment of the invention the acoustic energy generating element is a speaker having a power of 0.4 W, resistance of $4\Omega$, amplitude in the range of between about 4.2V to 7.36V peak to peak and a frequency range in the range of between about 300-700 Hz.

In embodiments of the invention the substrate is located substantially parallel to the filter.

In embodiments of the invention the substrate is located at the base of the filtration unit.

The substrate can be made of any suitable material which is capable of resonation in response to stimulation by the acoustic generating element. For example, this may be a metal, a ceramic or a polymer. Advantageously, because the substrate may come into contact with the fluid used in the apparatus the substrate is made of medical grade material. This reduces the risk of any toxic substance contamination.

The substrate may take the form of a soundboard or the like in the form of a composite panel with a layered or bonded sandwich construction. In a particularly preferred embodiment, the substrate comprises a polycarbonate (or other polymer) core and two outer metal layers or skins, which may be made of stainless steel. The outer skins or layers are very strong, while the inner core is lightweight and much weaker. The outer skins or layers are preferably thin, for example less than 0.1 mm and preferably less than 0.5 mm thick, while the inner core is thicker, preferably less than 1 mm thick, more preferably around 0.5 mm thick. The three layers are bonded to each other by high strength adhesive, for example an epoxy or methyl methacrylate adhesive. In some embodiments, the substrate is shaped as a disc, although polygonal and even conical shapes may be used in other embodiments.

The combination of a light polymer core (to minimise starting force requirements), stiff metal skins (to prevent uncontrolled vibration) and good damping (to reduce continuation of vibrations when the acoustic generating element has stopped) provides surprising benefits not available when using a non-composite construction.

In embodiments of the invention the acoustic energy generating element is reversibly coupled to the substrate. This coupling can be achieved by a variety of means available to the person skilled in the art, for example the use of an adhesive. This is particularly advantageous if the filtration unit is designed to be disposable, because the acoustic element can be uncoupled and re-used on other units.

The movement of the fluid sample across the filter can be via passive movement resulting from gravitational forces. Alternatively the fluid sample can be actively moved across the filter by the application of a positive or a negative pressure. The flow rate of the fluid sample across the filter can be constant or variable.

In embodiments of the invention the fluid provided within the post-filtration chamber which is capable of transmitting an acoustic wave also acts as a washing fluid. In this embodiment, a positive pressure pump is provided which pushes the washing fluid from the post-filtration chamber through the filter to the pre-filtration chamber. At the same time a negative pressure pump is drawing fluid from the pre-filtration chamber to the post-filtration chamber. Thus, the fluid sample and the washing fluid are sequentially moved in opposing directions across the filter such that the net movement of the fluid sample is into the post-filtration chamber and the separated solid fraction is retained in the pre-filtration chamber.

In general terms, embodiments of the invention may be further provided with means for applying a first pressure to move fluid from the post-filtration chamber through the filter into the pre-filtration chamber, and means for applying a second pressure to move fluid from the pre-filtration chamber though the filter to the post-filtration chamber.

The sequential movement of the fluid sample and the washing fluid in opposing directions across the filter prevents fouling and clogging of the filter, further increasing the efficiency of the separation process. This sequential movement can be cyclical, with one phase of the cycle being the rapid back-flushing of the filter using the washing fluid and the second phase of the cycle being the forcing of fluid sample downwards through the filter. This cyclic process is continued in order to sufficiently reduce the sample volume whilst also retaining a sufficient volume of fluid above the filter such that the particulate fraction is retained in solution. Typically the sample volume is reduced by about 10-fold.

In further embodiments of the invention the filter itself is agitated during the separation process. This agitation can be achieved, for instance, by associating the filter with a moveable holder. Agitation can be in a vertical direction or a lateral direction or a combination thereof. In alternative embodiments of the invention the filter can be rotated.

Other means of additionally agitating the washing fluid and/or the fluid sample include using a rotating element (e.g. impeller or insert in the fluid), rotating the walls of the chamber, or rotating the walls of the chamber, wherein the walls of the chamber is provided with baffles or the use of an active chip.

A "fluid sample" is any fluid from which solid components are to be separated. A sample can be from any source, such as an organism, group of organisms from the same or different species, from the environment such as from a body or water or from the soil, or from a food source, or an industrial source. A sample can be a processed or unprocessed sample. A sample can be a gas or a liquid. A sample can be an extract, for example a liquid extract of a soil or food sample.

The apparatus is particularly suitable for liquids that are viscous and which have a higher tendency to foul the filter by forming a film or coat on the surface of the filter. Backwashing of washing fluid through the filter, and optionally the agitation of the fluid sample and/or the filter significantly reduces the fouling of the filter and also maintains the particulate fraction in solution in the pre-filtration sub-chamber.

The sample can be obtained from a subject. The subject can be any organism, such as an animal or a human. An animal can include any animal, such as a feral animal or domestic animal. A domestic animal can include for example a companion animal such as a dog or cat.

The sample can be a biological sample such as a blood sample, an effusion, a urine sample, semen, bone marrow aspirate, spinal fluid, a cell suspension from tissue, mucus, sputum or saliva. The biological sample can be obtained from any animal and is not limited to a biological sample from humans.

A "blood sample" as used herein refers to a processed or unprocessed blood sample, including cord blood samples, bone marrow aspirates, internal blood or peripheral blood and can be of any volume and can be from any subject such as an animal or human. A preferred subject is human.

The solid fraction to be separated from the biological fluid sample can comprise at least one cell fraction. The cell fraction preferably comprises a therapeutic cell, that is any cell that can have therapeutic or curative effects.

The cell fraction can comprise or consist of at least one white blood cell. A "white blood cell" is a leukocyte, or a cell of hematopoietic lineage that is not a reticulocyte or platelet and which can be found in the blood of an animal or human. Leukocytes can include natural killer cells ("NK cells"), and lymphocytes such as B lymphocytes ("B cells") or T lymphocytes ("T cells"). Leukocytes can also include phagocytic cells such as monocytes, macrophages, and granulocytes, including basophils, eosinophils and neutrophils. Leukocytes can also include mast cells.

The cell fraction can comprise or consist of at least one red blood cell. A "red blood cell" is an erythrocyte.

The cell fraction can comprise or consist of at least one neoplastic cell. A "neoplastic cell" refers to abnormal cells that have uncontrolled cellular proliferation and continue to grow after the stimuli that induced the new growth has been withdrawn. Neoplastic cells tend to show partial or complete lack of structural organisation and functional coordination with the normal tissue, and may be benign or malignant.

The cell fraction can comprise or consist of at least one malignant cell. A "malignant cell" refers to a cell having the property locally invasive and destructive growth and metastasis. Examples of malignant cells include, but are not limited to; leukemia cells, lymphoma cells, cancers cells of solid tumours, metastatic solid tumour cells (e.g. breast cancer cells, prostate cancer cells, lung cancer cells, colon cancer cells) in various body fluids including blood, bone marrow, ascistic fluids, urine, bronchial washes.

The cell fraction can comprise or consist of at least one cancerous cell. A "cancerous cell" refers to a cell that exhibits deregulated growth and, in most cases, has lost at least one of its differentiated properties, such as, but not limited to, characteristic morphology, non-migratory behaviour, cell-cell interaction, and cell-signalling behaviour, protein expression and secretion pattern etc.

The cell fraction can comprise or consist of at least one stem cell. A "stem cell" is an undifferentiated cell that can give rise, through one or more cell division cycles, to at least one differentiated cell type.

The cell fraction can comprise or consist of at least one progenitor cell. A "progenitor cell" is a committed but undifferentiated cell that can give rise, through one or more cell division cycles, to at least one differentiated cell type. Typically a stem cell gives rise to a progenitor cell through one or more cell divisions in response to a particular stimulus or set of stimuli and a progenitor gives rise to one or more differentiated cell types in response to a particular stimulus or set of stimuli.

Bone marrow (or medulla ossea) is the soft tissue found in the hollow interior of bones. There are two types of bone marrow: red marrow (also known as myeloid tissue) and yellow marrow. Red blood cells, platelets and most white blood cells arise in red marrow; some white blood cells develop in yellow marrow.

Bone marrow contains two types of stem cells: hematopoietic stem cells and mesenchymal stem cells. Stem cells are primal cells common to all multi-cellular organisms that retain the ability to renew themselves through cell division and can differentiate into a wide range of specialized cell types. Hematopoietic stem cells give rise to the three classes of blood cell that are found in the circulation: white blood cells (leukocytes), red blood cells (erythrocytes), and platelets (thrombocytes). Mesenchymal stem cells are found arrayed around the central sinus in the bone marrow and have the capability to differentiate into osteoblasts, chondrocytes, myocytes, and many other types of cell.

Whilst embryonic stem cells are true stem cells in that they are totipotent or pluripotent and show unlimited capacity for self-renewal, the adult stem cells within the bone marrow are more appropriately termed progenitor cells, which like stem cells have a capacity for self-renewal and differentiation, although far more limited. Progenitor cells are usually unipotent or multipotent rather than pluripotent.

Mesenchymal stem cells or MSCs, classically obtained from bone marrow are multipotent stem cells that can differentiate into a variety of cell types. Cell types that MSCs have been shown to differentiate into include osteoblasts, chondrocytes, myocytes, adipocytes and neuronal cells.

Bone marrow density can and does vary from patient to patient and there is no uniform viscosity to bone marrow. Younger patients often have a denser thicker marrow the result of more trabecular tissue in the cavity. This viscous marrow has a tendency to foul the filters within separation devices.

In embodiments of the invention the fluid sample is a bone marrow aspirate.

In further embodiments of the invention the fluid sample is a bone marrow aspirate and the solid fraction is a progenitor cell.

A "tissue" as used herein includes the four basic types of tissue present in all animals: epithelium, connective tissue, muscle tissue and nerve tissue.

Examples of connective tissue include skin, muscle, cartilage, bone, tendon, ligament, joint capsule and adipose tissue.

"Adipose tissue" as used herein is intended to mean fat and other sources of microvascular tissue in the body. Adipose tissue is a complex tissue containing multiple cell types including adipocytes, pericytes, fibroblasts, macrophages, stem cells and microvascular cells. As such adipose tissue is one of the most convenient sources of precursor cells in the body.

"Microvascular cells" as used herein is intended to mean cells which comprise the structure of the microvasculature, such as endothelial cells, smooth muscle cells and pericytes.

Adipose tissue can be harvested from an "adipose" depot within the body. Suitable depots include the epididymis, the interscapular fat pad or the infrapatellar fat pad (Hoffas fat pad). Alternatively, and potentially more conveniently, the adipose tissue can be a lipoaspirate resulting from a liposuction procedure.

Whilst a lipoaspirate can be directly introduced into the device of the present invention, fragments of adipose tissue require pre-processing. The tissue fragments are comminuted and/or enzymatically digested to release the cellular component of the tissue. This cellular component can then be suspended in a suitable carrier and introduced into the device.

It is envisaged that the lipoaspirate and/or cell suspension obtained above can undergo further processing prior to introduction into the device. For example, gravitational sedimentation and/or centrifugation can be used to separate large fat globules and adipocytes from the stromal fraction (comprising stem cells, endothelial cells and pericytes).

In embodiments of the invention in which a biological sample is being filtered the filtration unit can be coupled to an aspirator such that the fluid is transferred directly from the subject into the filtration unit. The filtration unit can be used in a sterile environment and this arrangement reduces the risk of contamination of the sample between removal of the sample from the patient and introduction into the filtration unit.

In alternative embodiments of the invention the solid fraction can consist of an etiological agent such as bacteria, fungus, protozoan, virus, parasite or prion that can infect a subject.

The sample can be an in vitro cell suspension.

The filter, which can also be referred to as a foil, can be manufactured of any material suitable for separating a solid fraction from a fluid sample in the method described in the present invention. The filter can be manufactured from a natural or a synthetic material or a combination thereof. Suitable materials, include, but are not limited to metals, metal alloys, ceramics or polymeric materials. Examples include polycarbonate (PLC), polyethylene terephthalate (PET), polyidide (PI), nickel and stainless steel. The materials are preferably medical grade materials. Suitable tracked etched filters are available from it4ip (Belgium). Suitable nickel foil filters are available from Tecan Limited (U.K).

In embodiments of the invention the filter is substantially planar. That is to say, the filter has a 2-dimensional profile wherein the diameter of the filter is greater than the height of the filter. Such a profile increases the potential surface area by which the filter is exposed to the fluid sample, thereby increasing the rate of filtration. The profile also minimises the potential for any solid matter to become clogged within the filter.

Examples of suitable thickness for the filter are 11, 23 and 50 microns. The thinner the filter the faster the rate of flow of fluid therethrough.

It is envisaged that filter can be provided with pores of the same diameter or varying diameter having the same geometry. Alternatively, the filter can be provided with pores of the same diameter with varying geometry. Alternatively still the filter can be provided with pores of varying diameter and varying geometry Suitable pore geometries include, but are not limited to; circular, ellipsoidal, square, rectangular or triangular in lateral cross-section.

The pores can be tapered. Tapering of the pores facilitates deformation of the cells under vacuum. Depending on the size of the pore at each end of the taper and the orientation of the taper, preferential selection of cells based on size can be achieved. In advantageous embodiments of the invention the narrowest point of the tapered pore is located at the upper surface of the filter. This arrangement allows smaller cells to flow through the pore whilst larger cells are retained above the filter. Conversely, it seems to make it more difficult during the backwash of washing fluid upwards through the filter for the cells in the post-filtration chamber to return through pores. It has been found that if the narrowest point of the pore is located at the lower surface of the filter cells have a tendency to enter the pore and deform in order to squeeze through the narrowest point.

In particular embodiments of the invention the pores have a diameter range of between about 1 micron and 12 micron.

In further embodiments of the invention the pores can be cylindrical in shape.

In further embodiments of the invention in which progenitor cells are separated from a bone marrow aspirate, a suitable filter is made of PET, has a thickness of 23 microns, a pore diameter of 3 microns and a pore density of 400,000 pores per $cm^2$. The optimal negative pressure generated by a vacuum pump to effectively "pull" the fluid through the filter is in the range of about −0.1 to −0.5 psi, more specifically -0.2 to −0.3 psi. Alternatively a positive pressure can be generated to effectively "push" the fluid through the filter. The optimal positive pressure generated by such a pump is in the range of about +0.1 to +0.5 psi, more specifically +0.2 to +0.3 psi The design of the filtration unit can be modified such that the aspect ratio of the pre-filtration chamber for the fluid sample is reduced thereby providing a larger surface area for filtration per unit volume.

In further embodiments of the invention, the pre-filtration chamber of the filtration unit is divided into multiple chambers which can be used to receive batch fluid samples presented as a well plate format.

Following filtration the remaining fluid sample, which comprises the separated (also referred to as a purified, enriched or concentrated) solid fraction, can be removed from the upper chamber of the filtration unit by suction, for example using a pipette and either stored or utilised. In other embodiments of the invention, particularly in embodiments in which the remaining fluid sample comprises a therapeutic cell fraction, the remaining fluid sample can be mixed with, for example, a hydrogel or a bone cement. In these embodiments the hydrogel or bone cement functions as a cell repository.

According to a second aspect of the invention there is provided a method of separating a solid fraction from a fluid sample, said method comprising the steps of;
i) introducing a fluid sample into the apparatus of the present invention;
ii) filtering the fluid sample; and
iii) removing the separated fraction from the pre-filtration chamber.

According to a third aspect of the invention there is provided a method of isolating or separating a therapeutic cell from a fluid sample using apparatus of the present invention.

In embodiments of the invention the fluid sample can be a biological sample such as a blood sample, an effusion, a urine sample, semen, bone marrow aspirate, spinal fluid, a cell suspension from tissue, mucus, sputum or saliva.

In embodiments of the invention the therapeutic cell is a progenitor cell.

According to a fourth aspect of the invention there is provided a method of isolating or separating a therapeutic cell from a bone marrow aspirate using apparatus of the present invention.

In embodiments of the invention the therapeutic cell is a progenitor cell.

The controller in embodiments of the present invention may include a Programmable Logic Controller (PLC) programmed to switch a vacuum pump and a backwashing pump on and off in cyclic rotation in a timed sequence. The vacuum pump draws the fluid sample downwards through the filter under negative pressure. The backwashing pump forces washing fluid upwards through the filter.

The filtration chamber and/or the filter can be disposable. The control unit can be disposable or a standalone dedicated unit. In other words, the entire apparatus (optionally including the controller) may be disposable (subject to environmental considerations, for example relating to the disposal or recycling of batteries and other potentially toxic components). Alternatively, the apparatus may be reused, with only the filter and/or the filtration chamber being disposed of between uses.

In a further aspect of the invention the isolated therapeutic cell(s) can be directly administered as a suspension into a site in need thereof. Alternatively, the cells can be combined with or associated with an appropriate carrier material, for example, a gel, a paste, a cement, a glue, a scaffold, a film, an implant or a dressing.

It is envisaged that the isolated therapeutic cells can be utilised in a range of medical applications, for humans and/or non-human animals to repair, regenerate and/or augment tissue function.

Examples of medical applications include orthopaedic, neurological, cardiovascular, dermatology, cosmetic surgery and dental.

It is envisaged that in certain embodiments of the invention the isolated therapeutic cells comprise mesenchymal stem cells. These cells are capable of differentiation into osteoblasts, chondrocytes, myocytes and adipocytes. A therapeutic fraction comprising mesenchymal stem cells can be used in orthopaedic indications, resulting from disease or injury, such as cartilage repair, bone repair (including fracture repair), spinal fusion, degenerative disc treatment (including annulus repair, nucleous populous augmentation, disc augmentation)

Functional endothelial progenitor cells (EPCs) are central to vasculogenesis and angiogenesis. EPCs have been shown to develop from bone marrow mononuclear cells in adult animals. It is therefore envisaged that in certain embodiments of the invention the isolated therapeutic cells comprise EPCs and this therapeutic fraction can be used in indications in which damaged or ischemic tissue requires repair, regeneration or vasculogenesis, such as peripheral vascular disease.

There are therefore provided methods for i) forming new blood vessels in a tissue in a subject, ii) increasing blood flow in a tissue in a subject, iii) treating diseased tissue in a subject, iv) increasing angiogenesis in a diseased tissue or v) preventing heart failure in a subject, all of said methods comprising the steps of:
a) isolating bone marrow mononuclear cells using the apparatus according to the present invention,
b) transplanting locally into the tissue an effective amount of the bone marrow mononuclear cells so as to form new blood vessels in the tissue.

In embodiments of the invention the bone marrow mononuclear cells are autologous.

The tissue into which the bone marrow mononuclear cells are transplanted includes and diseased or damaged tissue and any tissue in need of repair or regeneration, including but not limited to underpurfused tissue such as tissue found in chronic ischemia, and also cardiac muscle tissue, skeletal muscle tissue, brain tissue e.g. affected by stroke or AV malformations, coronary vessels, kidney, liver, organs of the gastrointestinal tract, muscle tissue afflicted by atrophy, including neurologically based muscle atrophy.

In embodiments of the invention the new blood vessels are capillaries and/or collateral blood vessels.

Embodiments of the present invention may further comprise tilt means to tilt at least the pre-filtration chamber so as to facilitate collection of the solid fraction.

The tilt means may be activated automatically upon completion of the separation process, as discussed in more detail below.

Efficient and aseptic retrieval of a thin film of biological fluid on a flat surface is often difficult using conventional methods, for example by syringe. It would be desirable to provide apparatus for facilitating such retrieval.

It is known, for example from PCT/GB2008/000704, to provide a separation apparatus in which a biological fluid is drawn through a porous filter using a vacuum pump and acoustic standing waves that help to keep the pores of the filter clear. For the separation to be successful, the filter surface should remain flat and horizontal. The final volume of the filtrand or residue remaining on the upper surface of the filter after separation can be small, often in the form of a thin film on the upper surface of the filter.

To maximise or improve efficiency of recovery of the filtrand or residue for collection into, for example, a syringe, it is necessary for a user to tilt the filter surface so that the filtrand or residue can pool at one edge of the filter surface. However, if the filter surface is tilted before the separation has progressed to a desired degree, the filtrand can still contain an unwanted amount of filtrate or solvent. Moreover, it is important not to disturb the filter surface before separation is complete, otherwise solid residue in the filtrand can be unevenly distributed across the filter surface, leading to unwanted variations in separation between different samples.

According to a fifth aspect of the present invention, which may be used in conjunction with or independently of the previous aspects, there is provided an apparatus for separating a fraction from a fluid sample, the apparatus comprising:
- a filtration unit including at least one filter which divides the filtration unit into a pre-filtration chamber for receiving the fluid sample and a post-filtration chamber for receiving a filtrate of the fluid sample;
- electronic means for measuring a degree of filtration and for generating a signal when a predetermined degree of filtration has been achieved;
- filter tilting means for tilting the filter from a first orientation relative to a horizontal plane to a second orientation relative to the horizontal plane;
- wherein the filter tilting means is operable to tilt the filter in response to the signal from the electronic means.

In particularly preferred embodiments, the filter tilting means, once operated, does not allow the filter to be returned to and retained in the first orientation relative to the horizontal plane.

Devices processing biological materials especially of human origin are often single use and disposable. This feature and variations thereof help to prevent the filter or processing surface to be returned to a level setting, thereby preventing accidental re-use of a filtration unit.

The electronic means. may measure a volume or level of fluid in the pre-filtration chamber and/or a volume or level of fluid in the post-filtration chamber. Alternatively, the electronic means may measure a time elapsed, or a weight or mass of fluid in one or other of the chambers. In some embodiments, the electronic means may be configured to measure a degree of turbidity in the fluid in the pre-filtration chamber.

Advantageously, the filter tilting means automatically tilts the filter in response to the signal from the electronic means without requiring manual intervention from an operator.

In some embodiments, just the filter of the filtration unit is tilted, with the pre- and post-filtration chambers remaining generally stationary.

In other embodiments, the filtration unit is mounted on a base or in a housing, and the whole filtration unit, including the filter, is tilted relative to the base or housing, which remains generally stationary.

Advantageously, the filtration unit, or at least the filter, is provided with resilient or spring-loaded means for urging the filtration unit, or at least the filter, towards the second orientation from the first orientation. There is also then provided retaining means for holding the filtration unit, or at least the filter, in the first orientation against a force applied by the resilient means. The resilient means may comprise at least one compression spring, which may be a helical or leaf spring, or may comprise a resilient polymer, plastics or rubber component which, when compressed, generates an opposing elastic force. Alternatively or in addition, the resilient means may comprise at least one tension spring or component arranged to urge the filtration unit, or at least the filter, from the first orientation to the second orientation.

The retaining means, which forms part of the filter tilting means, is configured to release the filtration unit, or at least the filter, in response to the signal from the electronic means indicating that a desired degree of filtration has taken place. The filtration unit, or at least the filter, will then be moved by the resilient means from the first orientation to the second orientation.

In the first orientation, the filter is preferably arranged such that its surface facing the pre-filtration chamber is substantially horizontal with respect to a direction of action of gravity.

In the second orientation, the filter is preferably arranged such that its surface facing the pre-filtration chamber is tilted with respect to the horizontal, generally by an angle of less than 90°, typically less than 45°, and in some embodiments less than 30° or less than 10° or even less than 5°.

By tilting the filter surface, filtrand or residue in the pre-filtration chamber is caused to pool at a lower edge of the filter surface, thereby facilitating its removal, for example by way of a syringe.

The filtration unit may be hingedly mounted on the base or in the housing, where provided. Alternatively, the filter may be hingedly mounted in the filtration unit. The hinge allows the filter and/or the filtration unit to move between the first and second orientations.

Advantageously, the tilting means is configured so as to lock the filtration unit, or at least the filter, in the second (tilted) orientation after activation by the electronic means. This is so as to help prevent re-use of the filter or the filtration unit.

The retaining means may comprise a thread or filament of an appropriate natural or synthetic material that may be integral to or associated with a resistor or other electronic component, which may be provided on a printed circuit board (PCB). The thread or filament, which may be electrically conductive or may be an electrical insulator, is attached at one end to a part of the filtration unit, or at least the filter, and at the other end to a part of the base or housing or some other component relative to which the filter can move when moving from its first to its second orientation. The thread is arranged to hold the filter in its first orientation, for example by holding the filtration unit in place on the base or in the housing against the force applied by the resilient means. When the electronic means generates the signal, for example when a load cell or the like determines that a predetermined volume of filtrate or filtrand has been collected, the signal is used to cause the thread to break, thus allowing the filter to move to its second orientation.

Where the thread or filament is electrically conductive, the signal may cause an electrical current to flow in the thread or filament, causing it to heat up and then break (in the manner of a fuse wire).

In a particularly preferred embodiment, the retaining means comprises a fusible resistor incorporating a conductive filament.

Other arrangements for breaking the thread or filament may be provided.

Alternatively, the filter tilting means may comprise an electric motor, such as a servo motor, and/or an actuated mechanical or electromechanical screw.

In other embodiments, a hydraulically or pneumatically operated mechanism may be provided, for example a compressed air piston.

Alternatively, an electromagnet may be provided to hold the filtration unit, or at least the filter, in the first orientation, and the signal may cause the electromagnet to switch off and release the filtration unit, or at least the filter, so as to allow it to move to the second orientation.

In yet further embodiments, an electric field actuator may be employed.

In some embodiments, a counter balance weight may be used to move the filtration unit, or at least the filter, from the first to the second orientation.

Multiple resilient means or actuator springs can be used for more effective and controlled pop-up/tilting.

Bearings and/or dampers can be added to slow or smooth the tilting action.

In yet further embodiments, the apparatus includes a base or housing, and the entire base or housing, including the filtration unit and filter, is tilted relative to a (generally horizontal) surface upon which the base or housing is located. In these embodiments, the filter tilting means may comprise at least one moveable element such as an arm, leg, foot, lever or other member that is moveable from a first position, in which the base or housing sits flat upon the surface, to a second position, in which the base or housing is tilted relative to the surface.

The at least one moveable element is preferably provided with locking means to cause the element to be locked in the second position once it has moved a predetermined amount from the first position.

According to a sixth aspect of the present invention, which may be used in conjunction with or independently of the previous aspects, there is provided an apparatus for separating a fraction from a fluid sample, the apparatus comprising:
 a filtration unit including at least one filter which divides the filtration unit into a pre-filtration chamber for receiving the fluid sample and a post-filtration chamber for receiving a filtrate of the fluid sample;
 and filter tilting means for tilting the filter from a first orientation relative to a horizontal plane to a second orientation relative to the horizontal plane.

In embodiments according to this aspect, the filter tilting means may be manually operable by a user of the apparatus when it is determined that filtration has proceeded to a required degree. In other words, the filter tilting means in these embodiments is not necessarily activated automatically by electronic means.

In particularly preferred embodiments, the filter tilting means, once operated, does not allow the filter to be returned to and retained in the first orientation relative to the horizontal plane.

In some embodiments, just the filter of the filtration unit is tilted, with the pre- and post-filtration chambers remaining generally stationary.

In other embodiments, the filtration unit is mounted on a base or in a housing, and the whole filtration unit, including the filter, is tilted relative to the base or housing, which remains generally stationary.

In the first orientation, the filter is preferably arranged such that its surface facing the pre-filtration chamber is substantially horizontal with respect to a direction of action of gravity.

In the second orientation, the filter is preferably arranged such that its surface facing the pre-filtration chamber is tilted with respect to the horizontal, generally by an angle of less than 90°, typically less than 45°, and in some embodiments less than 30° or less than 10° or even less than 5°.

By tilting the filter surface, filtrand or residue in the pre-filtration chamber is caused to pool at a lower edge of the filter surface, thereby facilitating its removal, for example by way of a syringe.

The filtration unit may be hingedly mounted on the base or in the housing, where provided. Alternatively, the filter may be hingedly mounted in the filtration unit. The hinge allows the filter and/or the filtration unit to move between the first and second orientations.

Advantageously, the tilting means is configured so as to lock the filtration unit, or at least the filter, in the second (tilted) orientation when this is engaged. This is so as to help prevent re-use of the filter or the filtration unit.

In yet further embodiments, the apparatus includes a base or housing, and the entire base or housing, including the filtration unit and filter, is tilted relative to a (generally horizontal) surface upon which the base or housing is located. In these embodiments, the filter tilting means may comprise at least one moveable element such as an arm, leg, foot, lever or other member that is moveable from a first position, in which the base or housing sits flat upon the surface, to a second position, in which the base or housing is tilted relative to the surface.

The at least one moveable element is preferably provided with locking means to cause the element to be locked in the second position once it has moved a predetermined amount from the first position.

In some embodiments, the moveable element is recessed into the base or housing when in the first position, and projects from the base or housing, preferably from a bottom of the base or housing, when in the second position.

The moveable element may comprise an arm that is hingedly attached to the base or housing, for example at or near opposed edge portions of the base or housing. Alternatively, the moveable element may be slidably mounted in the base or housing. In some embodiments, the moveable element is spring-loaded so as to be urged towards the second position from the first position, but held in the first position until appropriate release means are activated by a user.

The moveable element may take the form of at least one rotatable foot or block, for example a wedge-shaped foot or block, which can be rotated through, for example, 180° or some other angle so as to cause the base or housing to be tilted relative to a surface on which it is disposed. Alternatively, the rotatable foot or block may be screw-mounted in the base or housing such that rotating the foot or block causes it to extend from the bottom of the base or housing.

Alternatively or in addition, at least one slideable foot or block may be provided on the base or housing.

Embodiments of the present invention may be used in combination with separation systems such as those described in PCT/GB2008/000704 which employ acoustic vibrations to keep a filter from becoming blocked, but may also be used in systems where no acoustic vibrations are applied.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

For a better understanding of the present invention and to show how it may be carried into effect, reference shall now be made by way of example to the accompanying drawings, in which.

DETAILED DESCRIPTION

Figure 1:
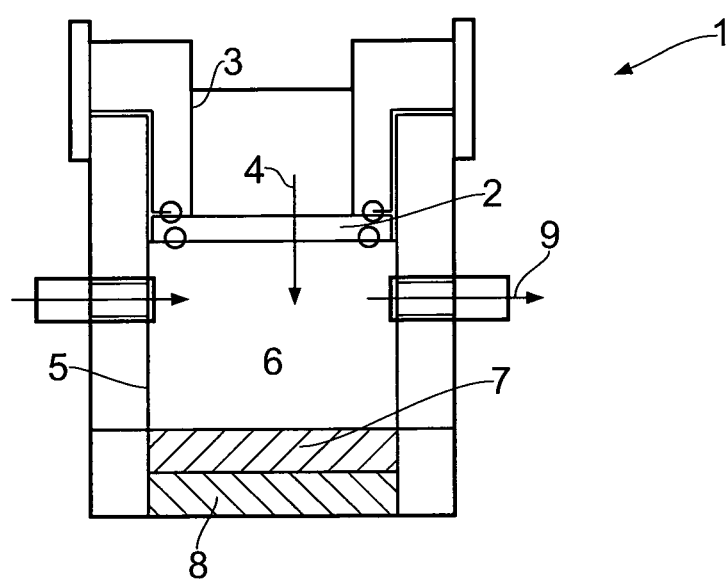
FIG. 1: A schematic showing the general operating principle of a filtration unit of the type incorporated in embodiments of the invention.

FIG. 1: A schematic showing the general operating principle of a separator apparatus of a type incorporated in embodiments of the present invention in which the following reference numerals refer:
1. Filtration unit
2. Porous filter
3. Upper (pre-filtration) chamber for receiving fluid sample.
4. Fluid sample
5. Lower (post-filtration) chamber for receiving back-flushing fluid.
6. Fluid provided in the post-filtration chamber
7. Resonating substrate
8. Acoustic energy generating element
9. Vacuum draw (optional)

The porous filter 2 separates a filtration unit 1 into two chambers; an upper (pre-filtration) chamber 3 into which a fluid sample 4 requiring cell separation is introduced and a lower (post-filtration) chamber 5 into which a fluid 6 capable of transmitting an acoustic standing wave is introduced. An acoustic element 8 is coupled to a substrate 7 which is located within and at the bottom of the lower chamber and which resonates in response to the acoustic generating element and generates a standing wave through the two fluid phases and the filter to agitate the sample. Simultaneously, a cyclic process of vacuum draw 9 causes movement of the sample downwards through the filter. Vacuum pressure, fluid flow rate and frequency of vibration are controlled by a controller (associated with appropriate pumps and valves. A concentrated fraction of desired larger cells is retained on top of the filter whilst smaller cells pass through the filter to a waste receptacle (not shown).

In a specific embodiment of the invention the acoustic element is a speaker having a power of 0.4 W, resistance of 4Ω, amplitude in the range of between about 4.2V to 7.36V peak to peak and a frequency range in the range of between about 300-700 Hz.

Figure 2:
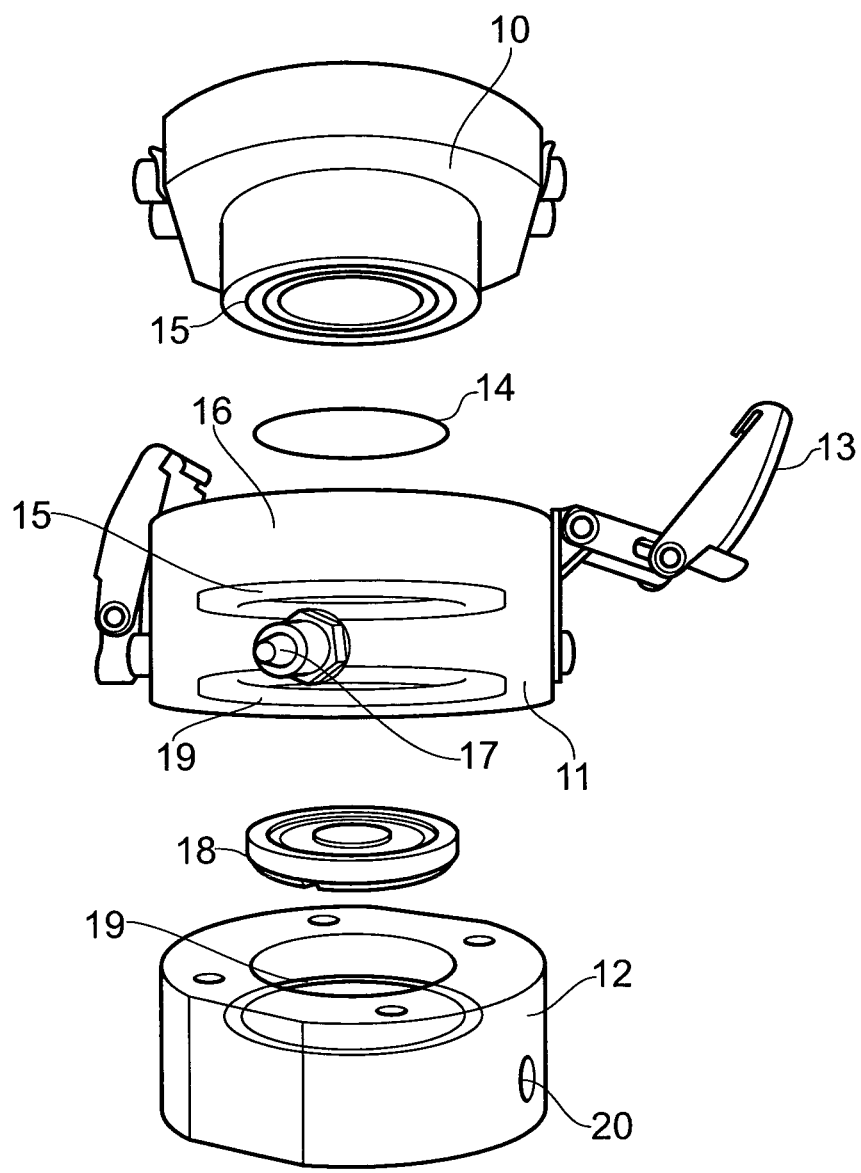
FIG. 2: A photograph of an embodiment of the filtration unit according to the invention.
Figure 3:
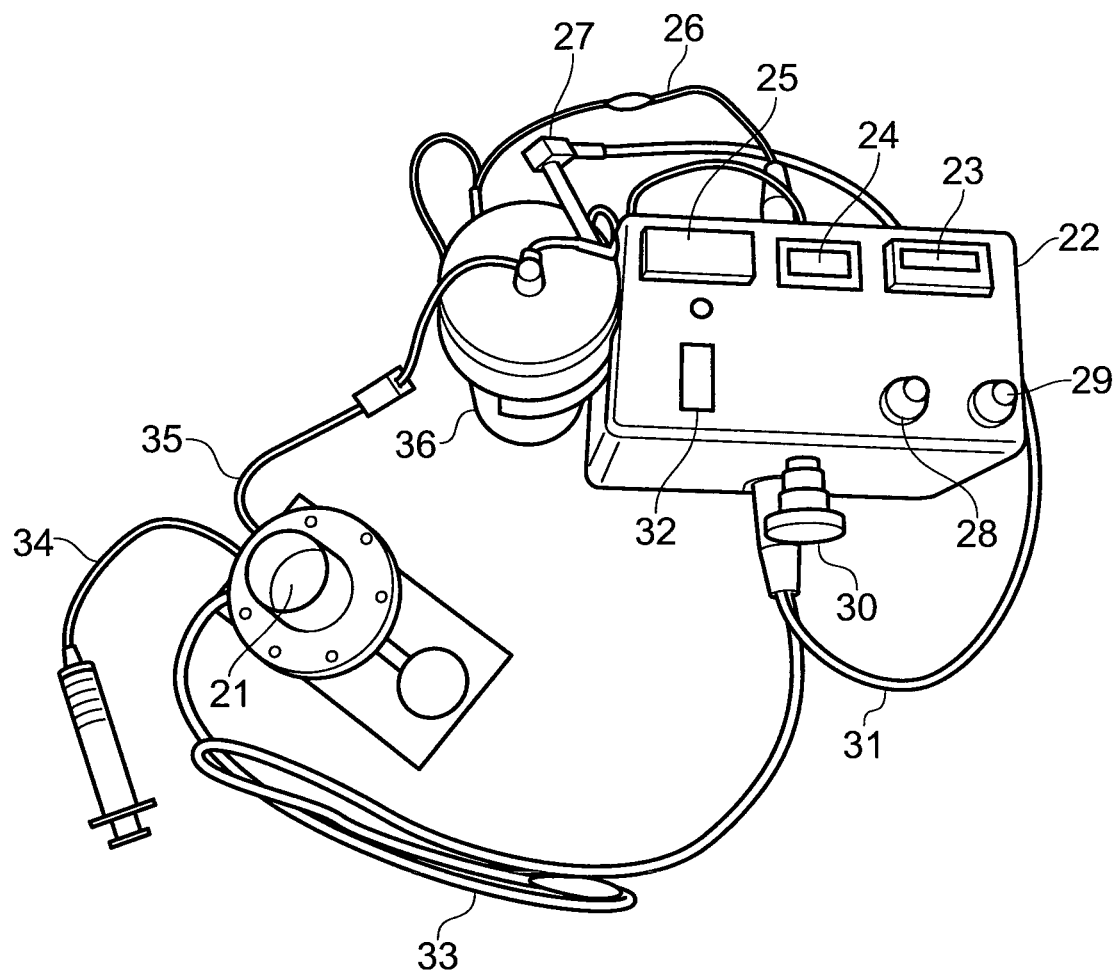
FIG. 3: A photograph of an embodiment of the separation apparatus according to the invention.

FIG. 2: A photograph of illustrating the component assembly of an embodiment of the filtration unit of the invention in which the following reference numerals refer:
10. upper chamber
11. middle chamber
12. lower chamber
13. clamps to secure upper chamber and middle chambers
14. membrane filter
15. O-rings sealing to filter when the upper and middle chambers are clamped together
16. upper tissue sample reservoir within middle chamber
17. input into saline reservoir below filter
18. acoustic energy generating element
19. O-rings sealing to acoustic element
20. exit for acoustic element electrical connection FIG. 3: A photograph of a separation apparatus of a type incorporated in embodiments of the present invention in which the fluids in the pre- and post-filtration chambers are sequentially moved across the filter, and in which the following reference numerals refer:

21. Filtration unit (process chamber)
22. Control unit
23. LCD: Acoustic frequency
24. LCD: Vacuum pressure
25. Drip counter
26. Drip sensor cable
27. Pressure sensor
28. Signal volume
29. Acoustic frequency
30. Vacuum knob
31. Pressure sensor cable
32. Pump switch
33. Audio cable
34. Saline line (from syringe to process chamber)
35. Waste line (from process chamber to waste chamber)
36. Waste chamber This figure illustrates an apparatus which comprises a filtration unit 21 and a control unit 22. The control unit 19 can be programmed to control the vacuum pump (Koge KPV14A-6A) (not shown). An amplifier and signal generator chip built into the control unit allows the frequency and amplitude of the acoustic element (not shown) to be set via the PLC. The PLC also operates together with a load cell (not shown) so as to vary the applied acoustic energy as the volume of fluid above the filter (not shown) changes, in accordance with aspects of the present invention.

Figure 4:
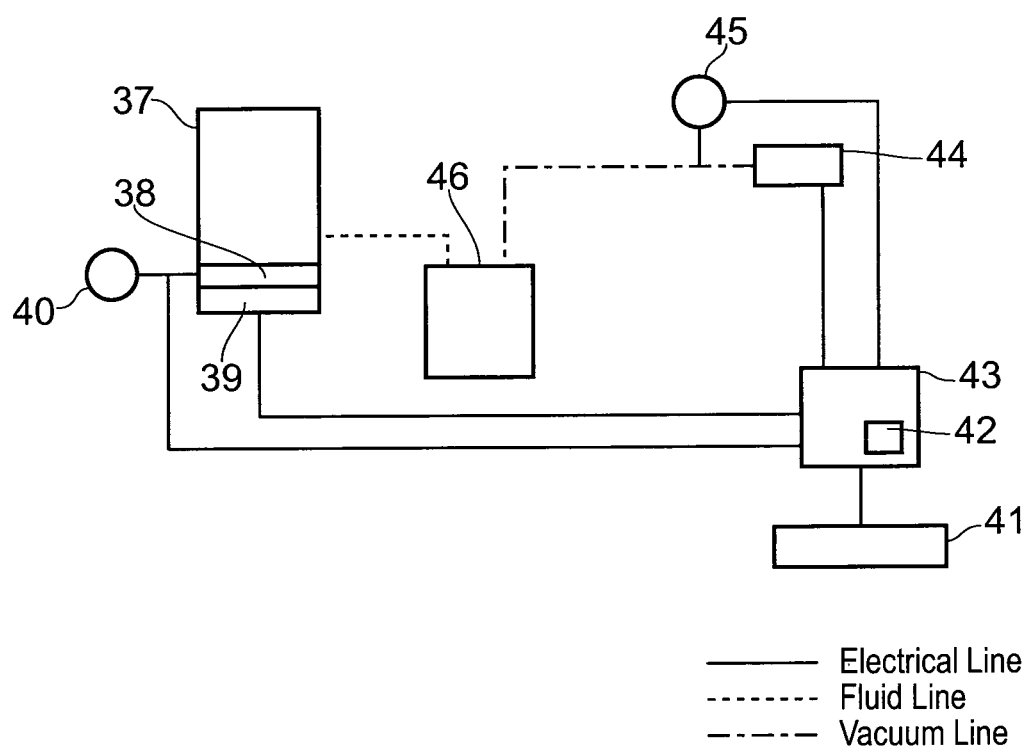
FIG. 4: A schematic of an embodiment of the separation apparatus according to the invention.

FIG. 4: Schematic representation of a further embodiment of the apparatus of the invention and in which the following reference numerals refer:

37. Filtration unit
38. Acoustic energy generating element
39. Load cell
40. Acoustic sensor
41. Interactive LDC panel—LCD user interface
42. Micro processor
43. Printed circuit board, PCB
44. Vacuum pump
45. Pressure sensor
46. Waste chamber The PCB 43 is programmed to switch the acoustic energy generating element 38 and vacuum pump 44 (Koge KPV14A-6A) on and off. It is also integrated with a pressure sensor 45 and an acoustic sensor 40 (e.g. microphone) to constantly monitor and adjust the working vacuum pressure and the acoustic energy to an optimum. The LCD interface 41 guides the user through the entire process/procedure with interactive flashing icons indicating what the user should do in each step. The entire system is powered up by a 'Power Source' e.g. batteries.

Figure 5:
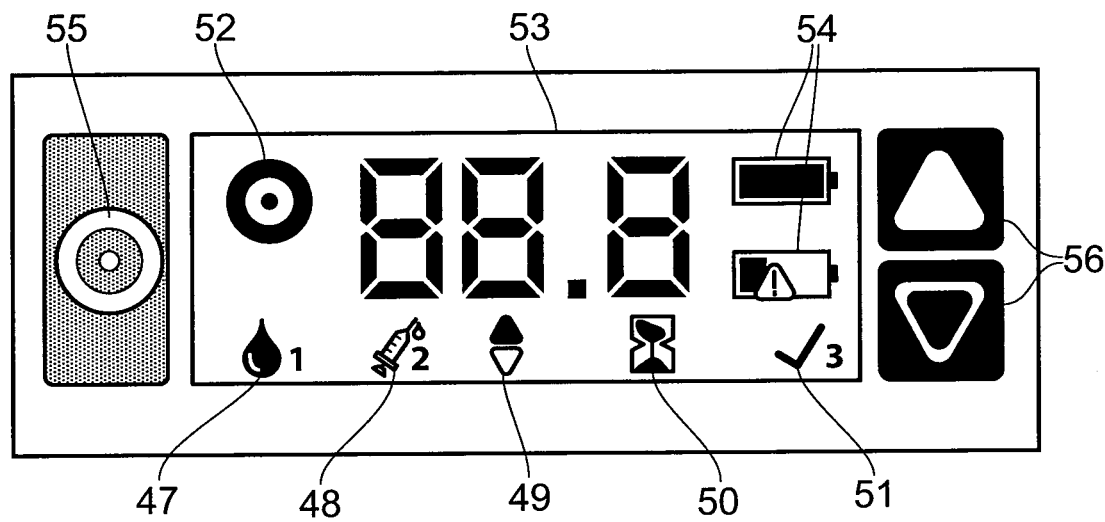
FIG. 5: A photograph of the LCD user interface on the control unit.

FIG. 5: Photograph of the LCD user interface on the control unit of the invention and in which the following reference numerals refer:

icons
47: input saline
48: input biological fluid
49: input required final volume
50: Processing
51. Required volume reached (processing completed)
52: Press set/next button
53: Fluid volume
54: Battery power indicator
action buttons
55: Set/next button
56: Up and down button for adjusting fluid volume.

In normal operation the separation chamber of the apparatus is initially free of fluid. The LCD interface will display 'Input Saline' 47 and 'Input Biological Fluid Mixture' 48 icons to indicate the user to deliver the fluids into apparatus. The volume of the biological fluid mixture added is registered by the load cell and displayed on the LCD 53. This will be followed by the 'Input Required End Volume' 49 icon which can be set by using the 'Up and Down Buttons' 56 on the panel. Once the required final volume is set the biological fluid mixture will undergo processing, which will be indicated by the 'Processing in Progress' 50 icon. During processing, the acoustic element and the vacuum pump are switched on. The acoustic energy and the vacuum pressure applied will be constantly monitored and automatically adjusted as the processing fluid volume decreases. The acoustic energy has amplitude fixed at 11V and an amplifier signal voltage of less than 5V. The signal volume range from 2 to 6 and the frequency range from 350 to 650 Hz, this drives a standing wave through the fluid and the fluid observed to be in constant agitation. The negative vacuum pressure applied range from 0.2 to 0.3 psi to keep a net unidirectional flow of biological fluid through the filter into the waste chamber. Once the desired/entered end volume is reached, 'Process completed' icon appears 51, and the PCB is permanently disabled with a 'kill' command form the micro-processor. The processed biological fluid above the filter is then removed and is ready for use.

Figure 6:
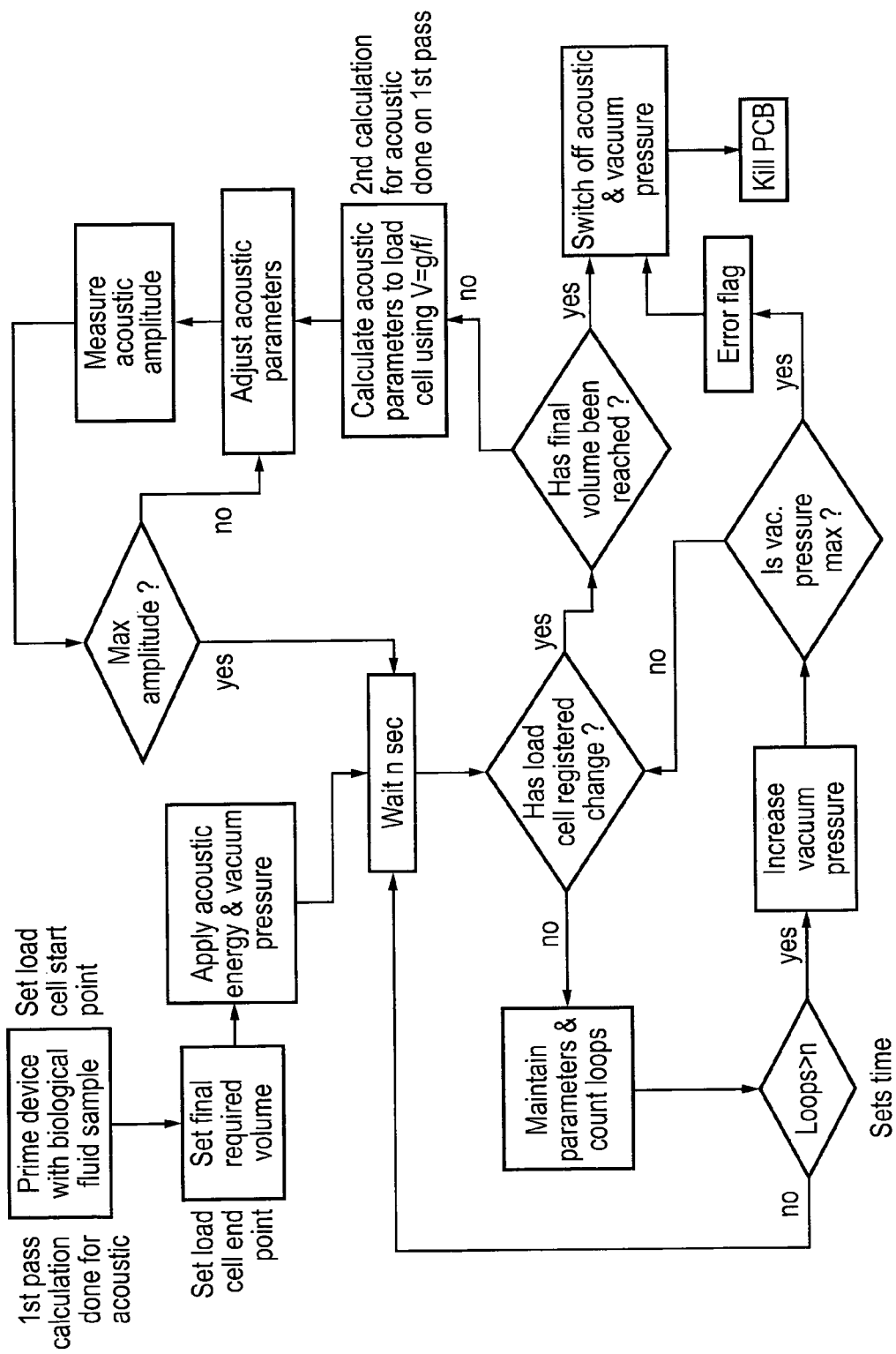
FIG. 6: A flow diagram showing a general operating principle of the controller and its connected components.
Figure 7:
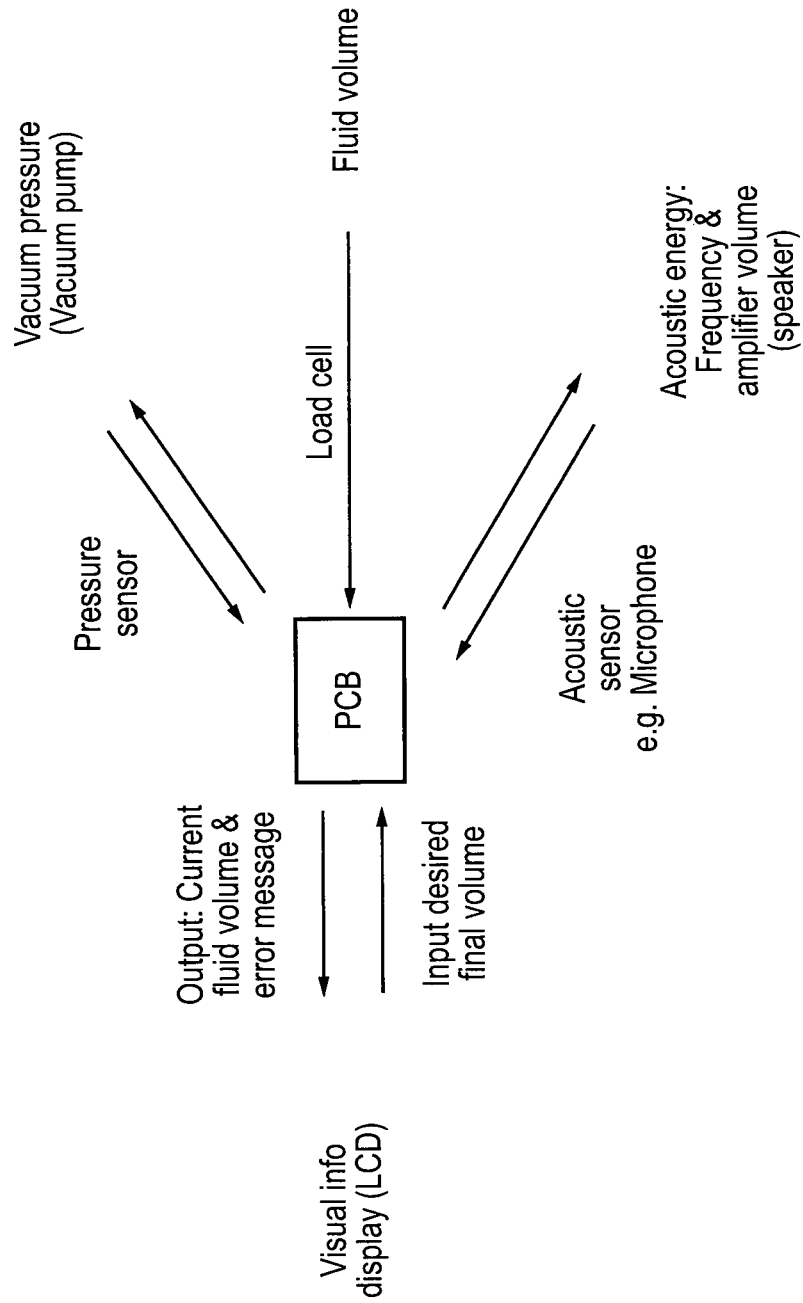
FIG. 7: A chart showing the role of the controller PCB in controlling, monitoring and regulating vacuum pressure, fluid volume/load and acoustic energy.

The flow diagram of FIG. 6 shows a currently preferred operating principle for the control system of embodiments of the present invention, with FIG. 7 showing the role of the PCB in controlling, monitoring and regulating the vacuum pressure, fluid volume/load and acoustic energy.

The separation apparatus of FIG. 4 has a load cell that measures the mass of the fluid and a microprocessor that controls the frequency of an acoustic actuator. The fluid mass above the porous filter in the separation chamber was recorded every 20 seconds, as well as the corresponding acoustic frequency at that time point.

Figure 8:
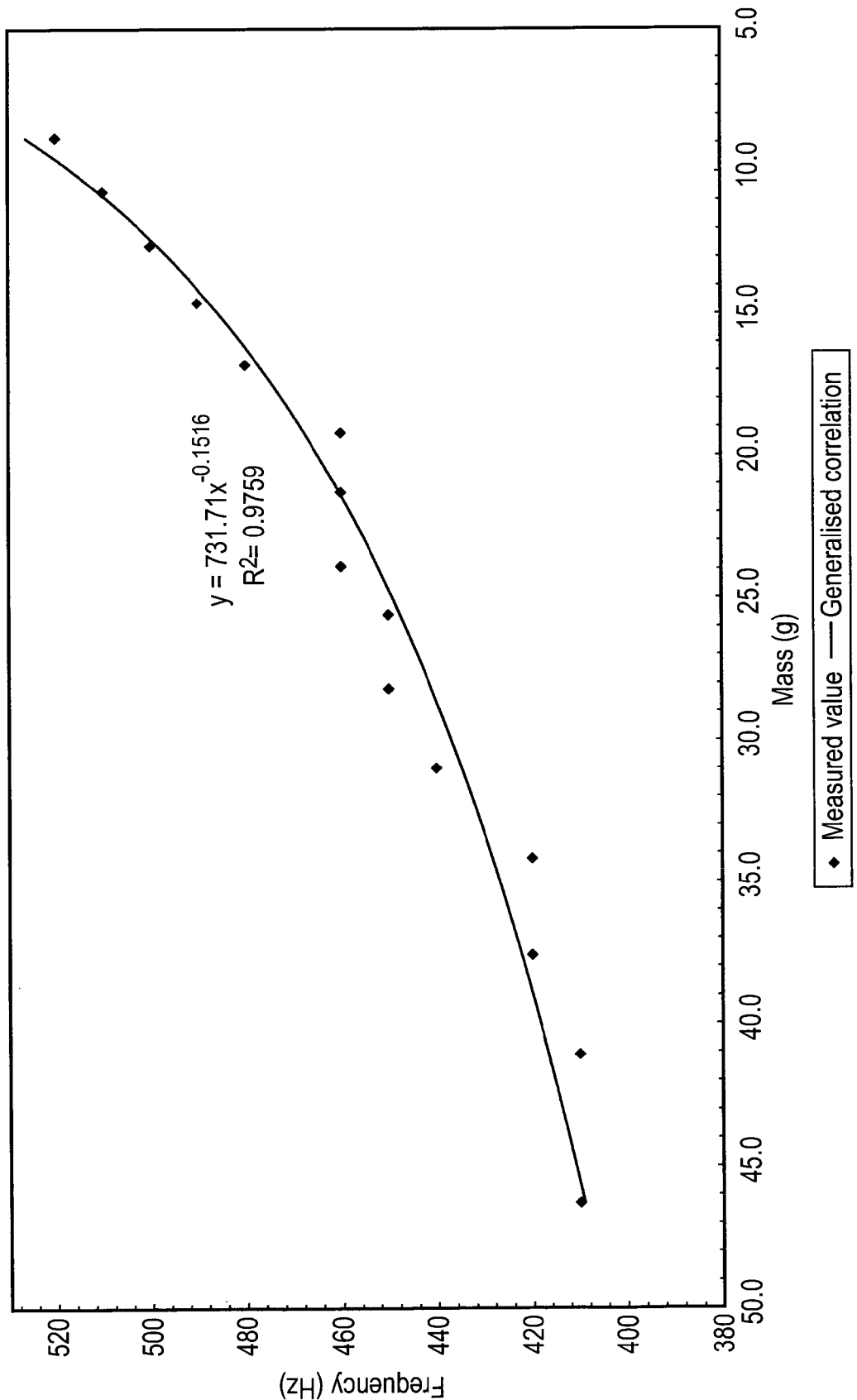
FIG. 8: A plot showing mass-frequency correlation in an embodiment of the present invention.

A representative mass-frequency profile is shown in FIG. 8 for the separation apparatus using porcine bone marrow. The measured data is best represented by the correlation:

$$y=733.12x(e-0.1516) \text{ with an } R^2=0.9759.$$

In practice, the generalised correlation would be applied within the microprocessor software, such that for a given measured fluid mass the appropriate frequency would be applied to the acoustic actuator in the separation apparatus.

Figure 9:
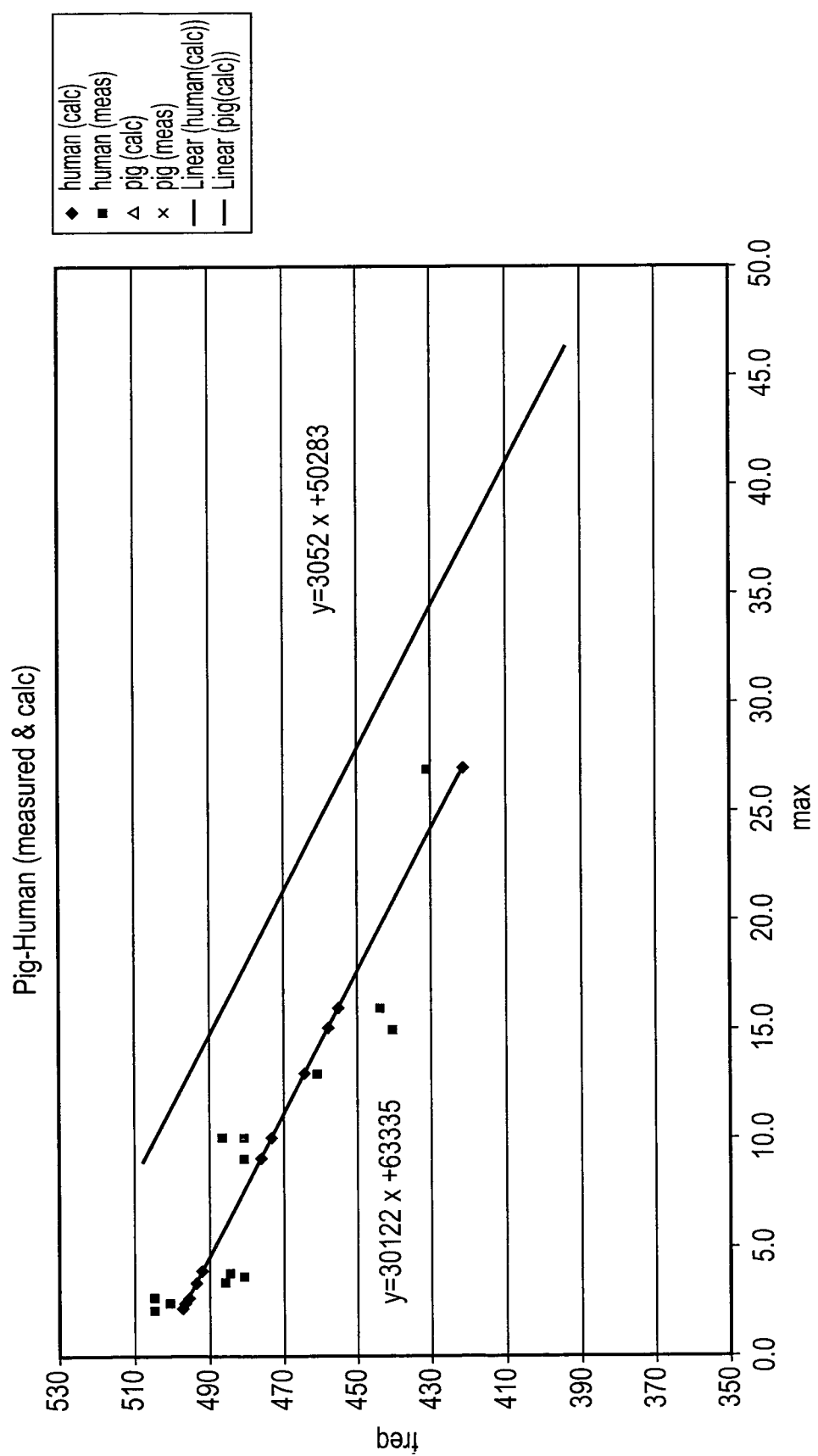
FIG. 9: A plot showing the measured and calculated correlations for acoustic frequency against mass in an embodiment of the present invention for both human and porcine bone marrow aspirate (BMA).

Another representative mass-frequency profile is shown in FIG. 9 for the separation apparatus of FIG. 8 using both human and porcine bone marrow aspirate (BMA). The measured data is best represented by the linear regressions:

$$y=-3.052x+502.83 \text{ (human BMA)}$$

$$y=-3.0122x+533.35 \text{ (porcine BMA)}$$

As fluid processing progressed, the mass of fluid contained above the filter was registered on an LCD coupled to a load cell. Simultaneously, the frequency of the acoustic element was registered on an independent LCD display. These data were generated using the same device.

The regressions show that irrespective of tissue type the same linear change in frequency correlates to the change in fluid volume. The data also suggests that for human tissue there is constant reduced offset in frequency of approximately 30 Hz.

Various materials may be used as a loudspeaker cone/diaphragm, but the most common are paper, plastic and metal. The ideal material would be light (to minimise starting force requirements), stiff (to prevent uncontrolled cone motions) and well damped (to reduce vibrations continuing after the signal has stopped). In practice, the three criteria cannot be met simultaneously using existing materials. As a result, many loudspeaker diaphragms are made of some sort of composite material.

Figure 10:
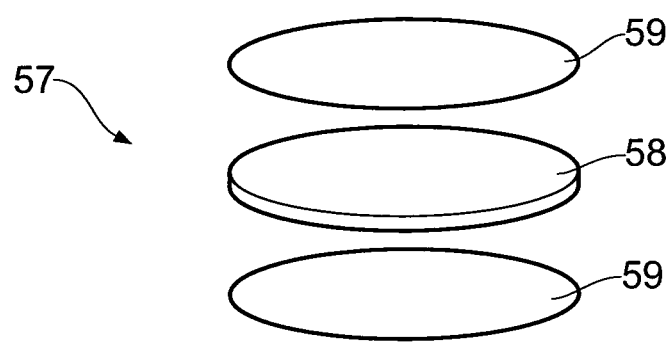
FIG. 10: An exploded view of a vibrating substrate suitable for use with embodiments of the present invention.

FIG. 10 shows an exploded view of a substrate or 'soundboard' 57 made of composite material that, when used as loudspeaker cone/diaphragm in combination with an acoustic energy generating element, is capable of delivering appropriate acoustic energy into the biological fluid. It is a composite panel with layered/bonded sandwich construction, consisting of a polycarbonate disc core 58 and two outer stainless steel skins 59 of specific thickness. The outer skins 59 are extremely strong and the core 58 is lightweight and very much weaker, but with the use of a suitable adhesive the benefits are realised. Details are shown in Table 1. This combination of materials gives the soundboard 57 a unique material stiffness and performance characteristic such that, when used as speaker cone/diaphragm in combination with an acoustic actuator, it generates fluid resonance through efficient acoustic energy delivery which in turn provides efficient filtering in the cell separation apparatus of embodiments of the present invention.

TABLE 1

|  | Detail | Supplier |
| --- | --- | --- |
| Core | 0.5 mm thick polycarbonate sheet | Fibrefusion Ltd (Cornwall, UK) |
| Skin | 0.05 mm thick 304 stainless steel sheet | Rayhome Ltd (Bury, UK) |
| Adhesive | Huntsman Araldite 2022 methyl methacrylate (or Araldite 2015 epoxy) | Huntsman Advanced Materials Americas Inc. (Texas, USA) |
| Manufacturing process | Heated platen lamination machinery | Fibrefusion Ltd (Cornwall, UK) |
| Size | Ø60 mm | — |

Figure 11:
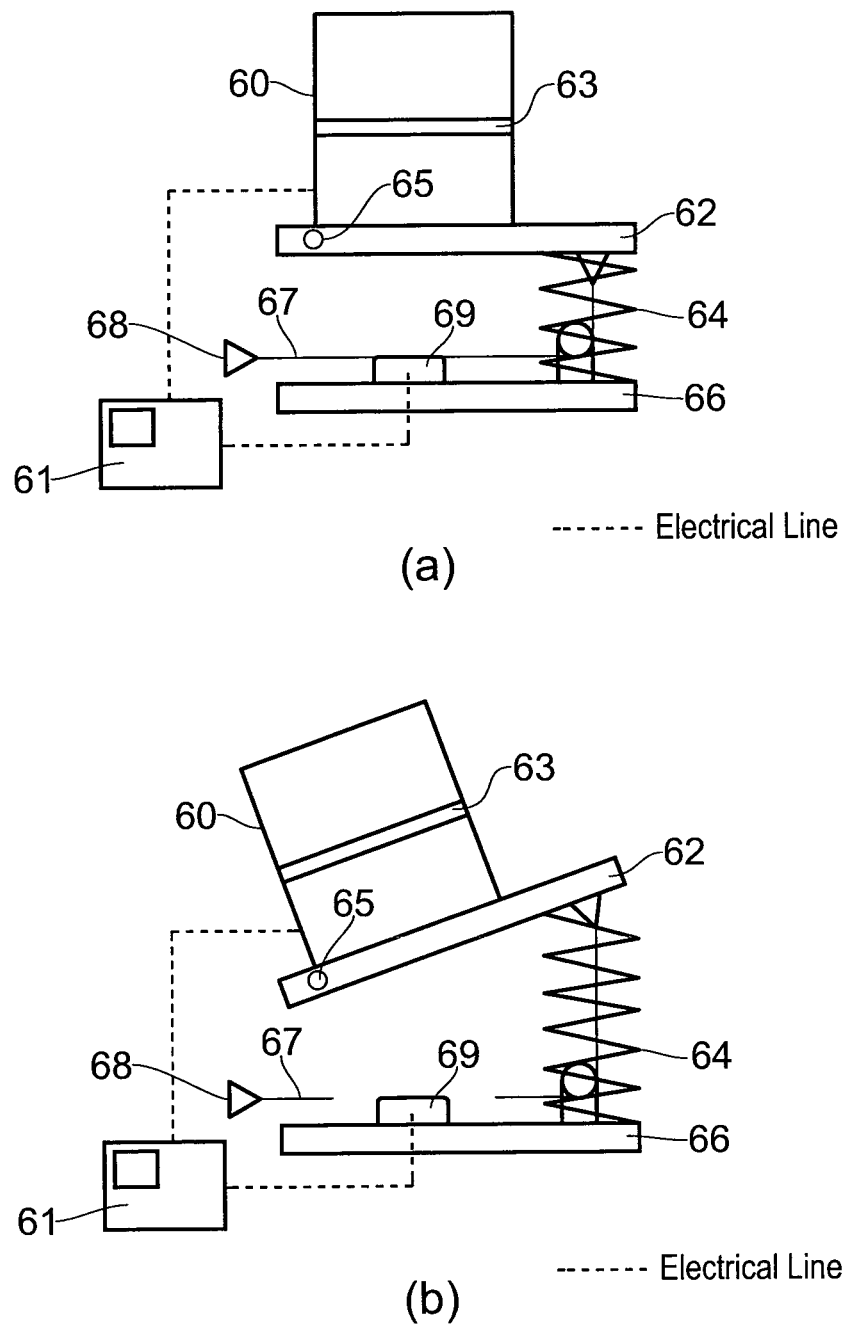
FIG. 11: A schematic view of embodiment of the apparatus incorporating an automatic tilt mechanism in (a) a first configuration and (b) a second configuration.

A current working embodiment of an alternative embodiment of the invention is schematically represented in FIG. 11 comprising hinged separation chamber 60 together and a PCB/microprocessor 61.

The hinged separating chamber is a pop-up sub-assembly held in a preloaded position as described below:

The hinged supporting platform 62 is a moulding that incorporates the separation chamber as well as keeping the separation chamber and the porous filter 63 in the horizontal position. It is designed to pop-up to desired tilt angle once the biological fluid processing is complete, thus allowing for maximum recovery of the processed fluid. The actuator spring 64 is located at the opposite end to the hinge 65 sandwiching between the hinged supporting platform 62 and the base 66. It provides a uniform elevation force on the hinged separating chamber. The spring is under compression when the assembly is in the preloaded position.

A fusible filament 67 (e.g. polymer filament loop) is tethered at one end to the hinged separation chamber (opposite to the hinge), drawn taut and tethered to the filament retainers 68 at the other end. This action anchors the separation chamber with the spring compressed such that the pop-up sub-assembly is grounded and preloaded. The filament is in direct contact with the fusible resistor 69 which, when activated, melts the filament and thereby allowing the preloaded subassembly to pop-up once processing is completed. The filament retainers hold the filament within the assembly by providing a method of attaching the filament to the pivoting bodies, whilst maintaining the tension in the filament in the preloaded position. The base provides the grounding points and guides for the filament to run through.

When the specified final volume is reached (i.e. processing completed) and recognised by the load cell of the separation chamber, it triggers the PCB/microprocessor to activate the fusible resistor such that the filament is melted and broken at the point of contact. Once the thread is broken, the compression springs serve to release the anchored separation chamber that then mechanically locks out into the desired tilt angle. This is shown in FIG. 11b.

Figure 12:
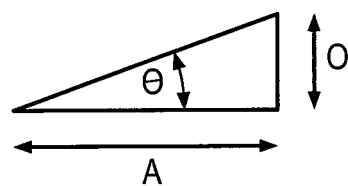
FIG. 12: A schematic diagram showing a relationship between tilt angle, hinge-to-spring distance and spring extension.
Figure 12:
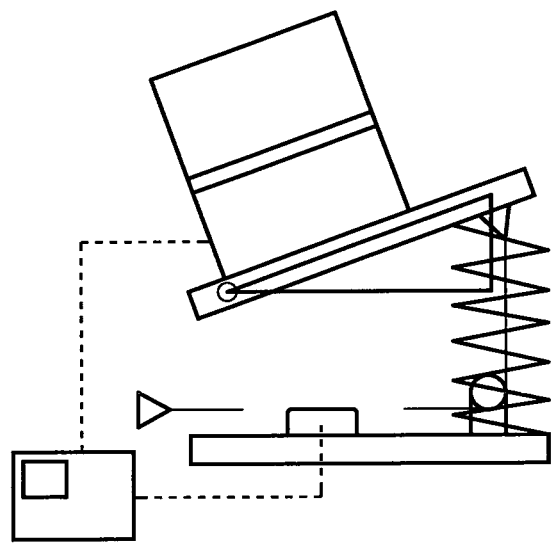
Figure 13:
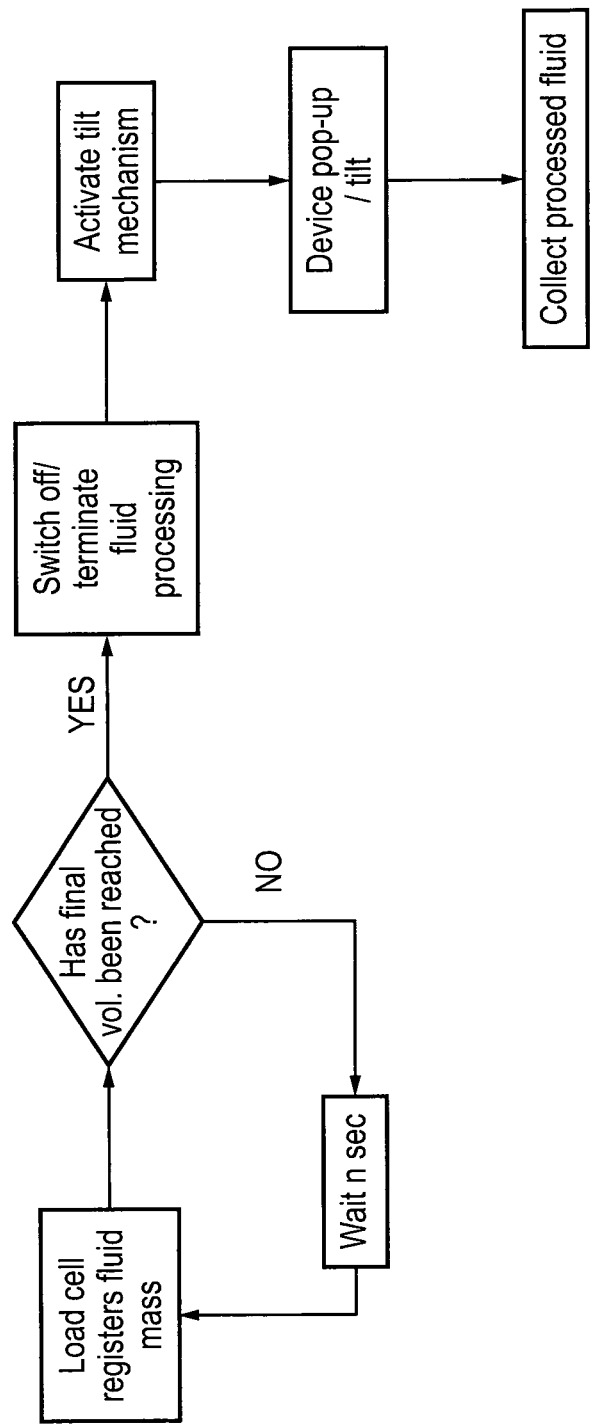
FIG. 13: A flow diagram showing a decision-making process used in embodiments illustrated in FIGS. 11 and 12.

The pre-set tilt angle is determined by (1) the uncompressed actuator spring length and (2) the position of the spring relative to the hinge (pivot point). This is demonstrated in FIG. 12, showing the relationship:

$$\text{Tilt angle } \theta = \tan^{-1}(O/A)$$

where:
$\theta$=Tilt angle
O=length of relaxed spring−length of compressed spring
A=distance between hinge and spring FIG. 13 is a flow chart showing a decision-making process used in embodiments of the present invention illustrated in FIGS. 11 and 12.

Figure 14:
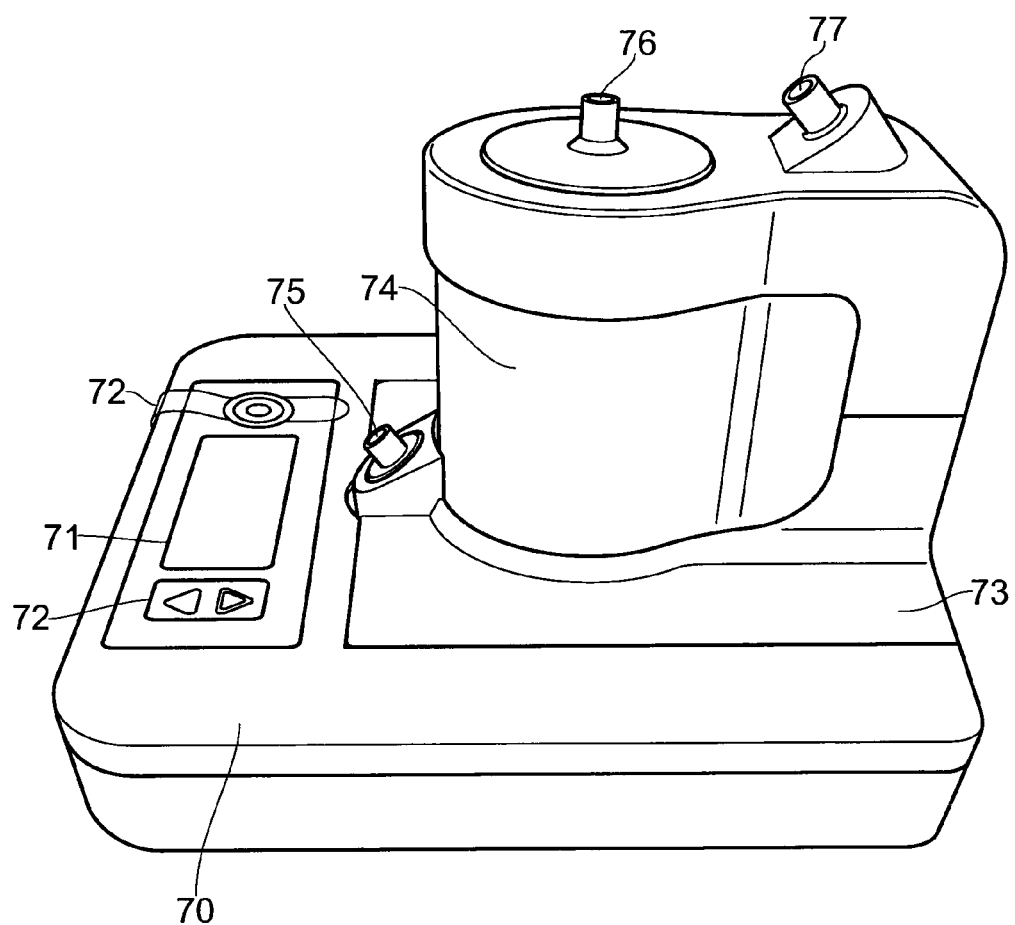
FIG. 14: A photograph of an embodiment of the apparatus utilising an automatic tilt mechanism. Shown in the pre-load configuration.
Figure 15:
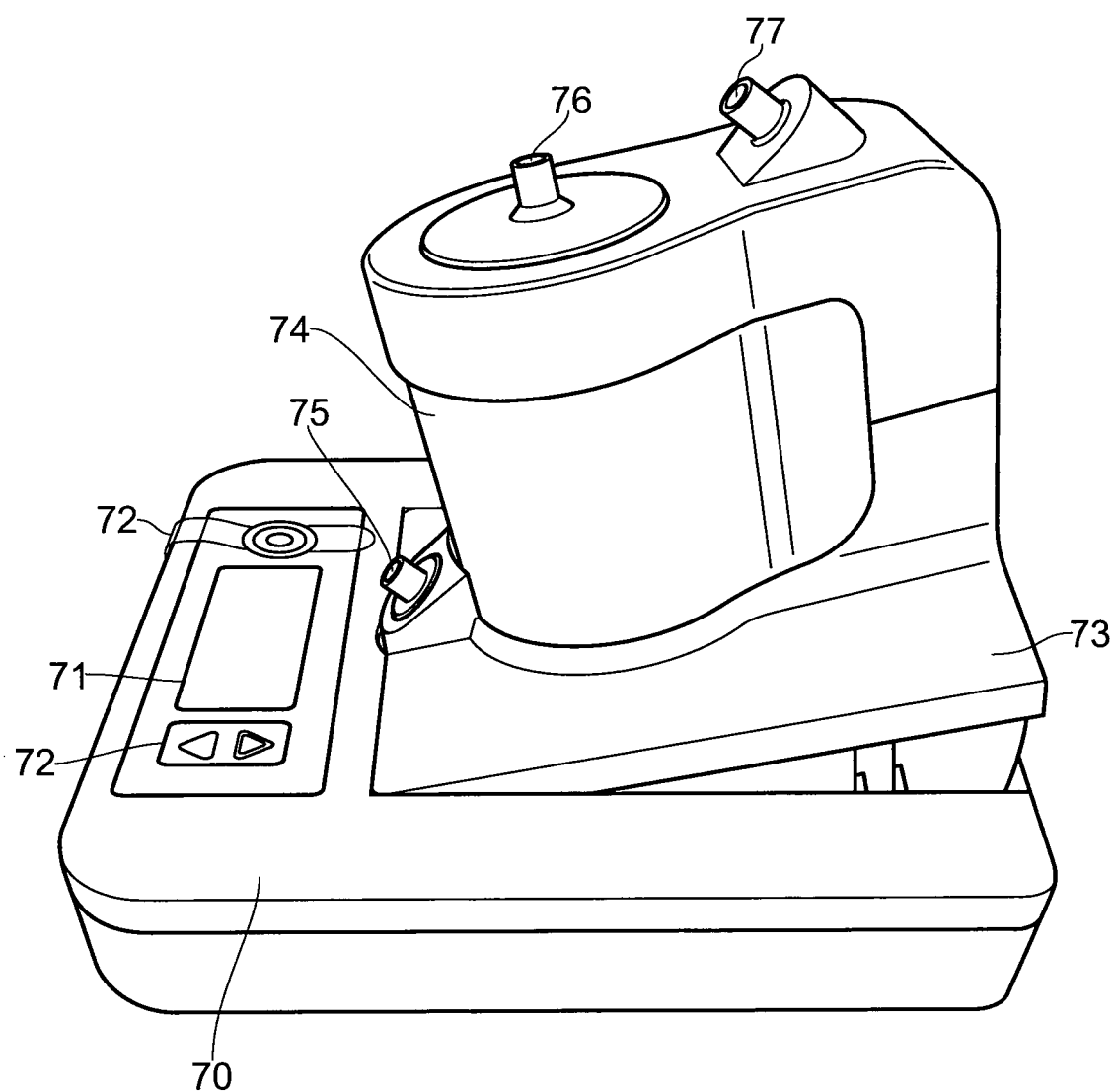
FIG. 15: A photograph of an embodiment of the apparatus utilising an automatic tilt mechanism. Shown in the tilted configuration.

FIGS. 14 and 15 illustrate an embodiment of the invention in its pre-load and automatically tilted configurations, respectively. The Figures show the base 70 which includes a display 71 and user controls 72, the hinged supporting platform 73, the separation chamber 74 an outlet port 75 to which a syringe (not shown) may be attached in order to take a sample of filtrand or residue, and input ports 76, 77. The hinged supporting platform and the separation chamber are preferably configured as a disposable unit incorporating the tether (not shown). Once the tether has been broken and the hinged platform has popped up into the tilted configuration of FIG. 15, the hinged platform cannot be locked back in the preload configuration of FIG. 14, thereby preventing accidental re-use of the unit, which might otherwise result in cross-contamination between clinical samples and/or patient tissue.

Figure 16:
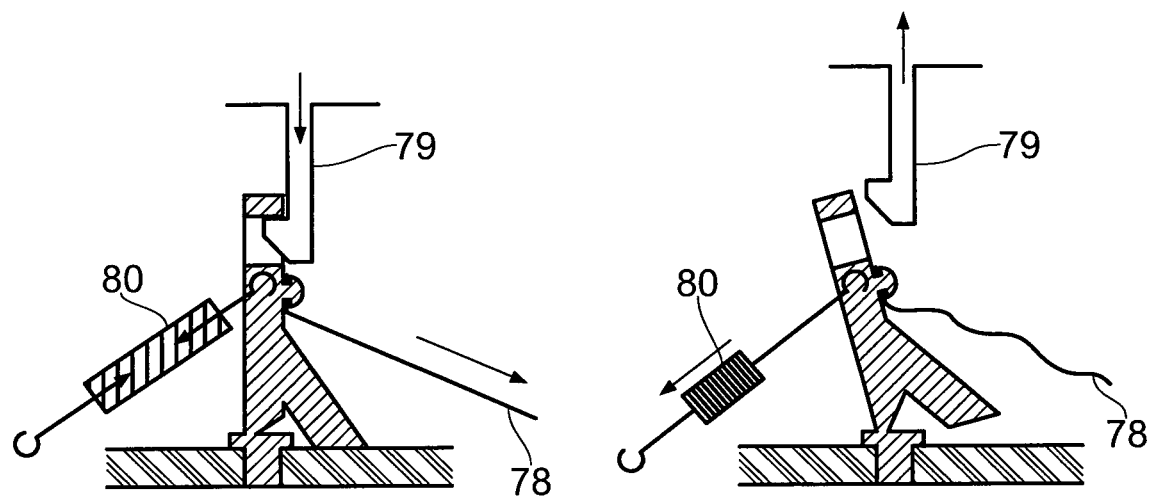
FIG. 16: A schematic view of an alternative embodiment of the apparatus incorporating an automatic tilt mechanism in a first and second configuration.

FIG. 16 shows an alternative embodiment in which the automatic tilt mechanism has been redesigned by using the filament or tether 78 to release a simple trigger mechanism instead of holding the full force of the sprung pivoting section. With this arrangement, the tether 78 would be only under a small amount of tension—just enough to overcome a small spring force. For example, a small pivoting trigger 79 (e.g. made from polypropylene with a living hinge) would be under tension from a small spring 80, and held in its 'set' position by the tether. When in the preload position, the pivoting section (e.g. a hook depending from the hinged supporting platform), would snap into place. When the tether is released, the trigger would be released and the pivoting section would pop-up.

FIGS. 17 to 24 show alternative embodiments of the apparatus utilising manually-operated tilt means.

Figure 17:
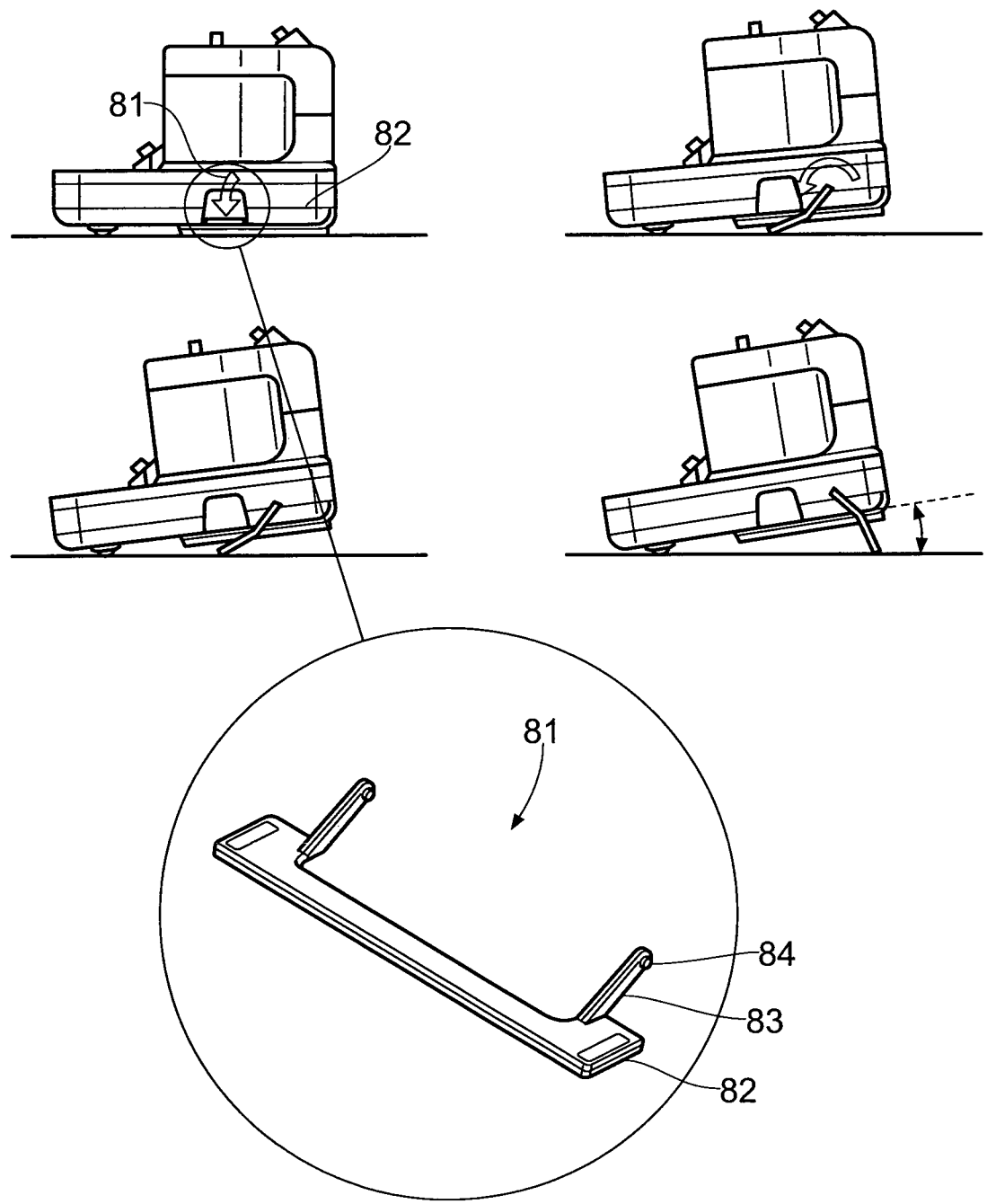
FIG. 17: A schematic view of an embodiment of the apparatus incorporating a mechanical tilt mechanism.
Figure 18:
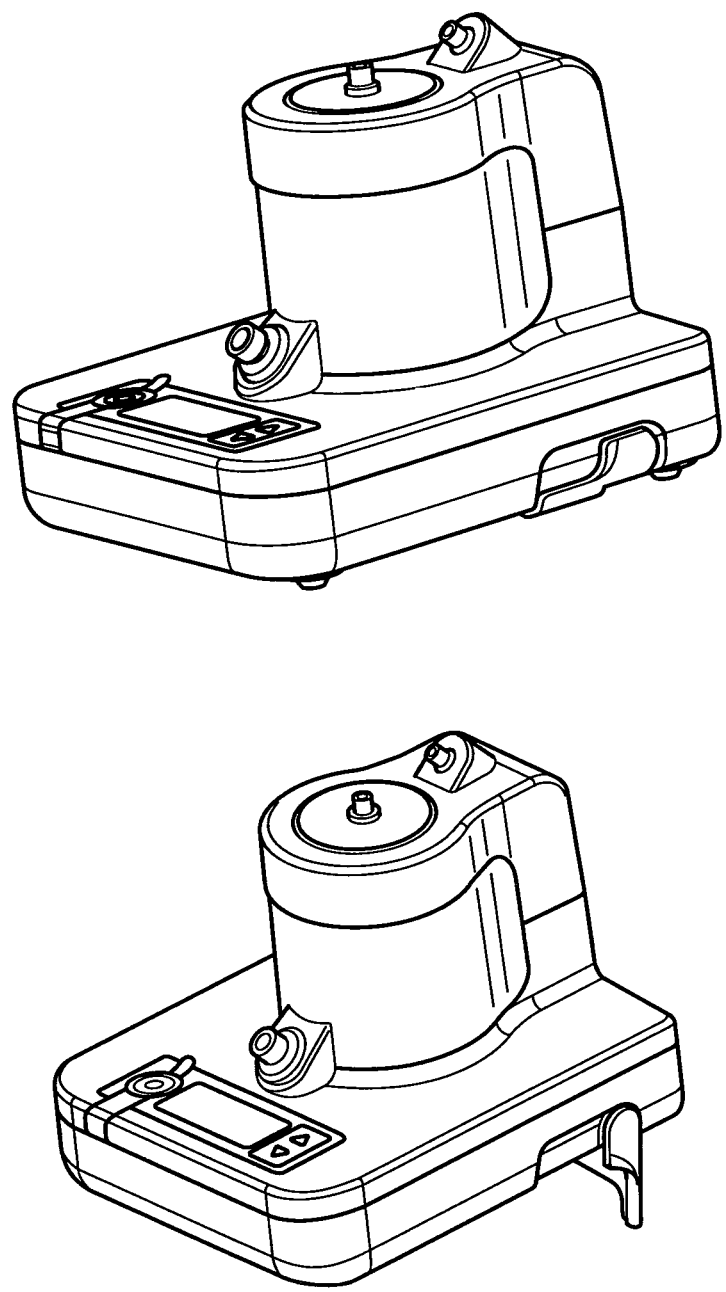
FIG. 18: A photograph of the embodiment illustrated in FIG. 17.
Figure 19:
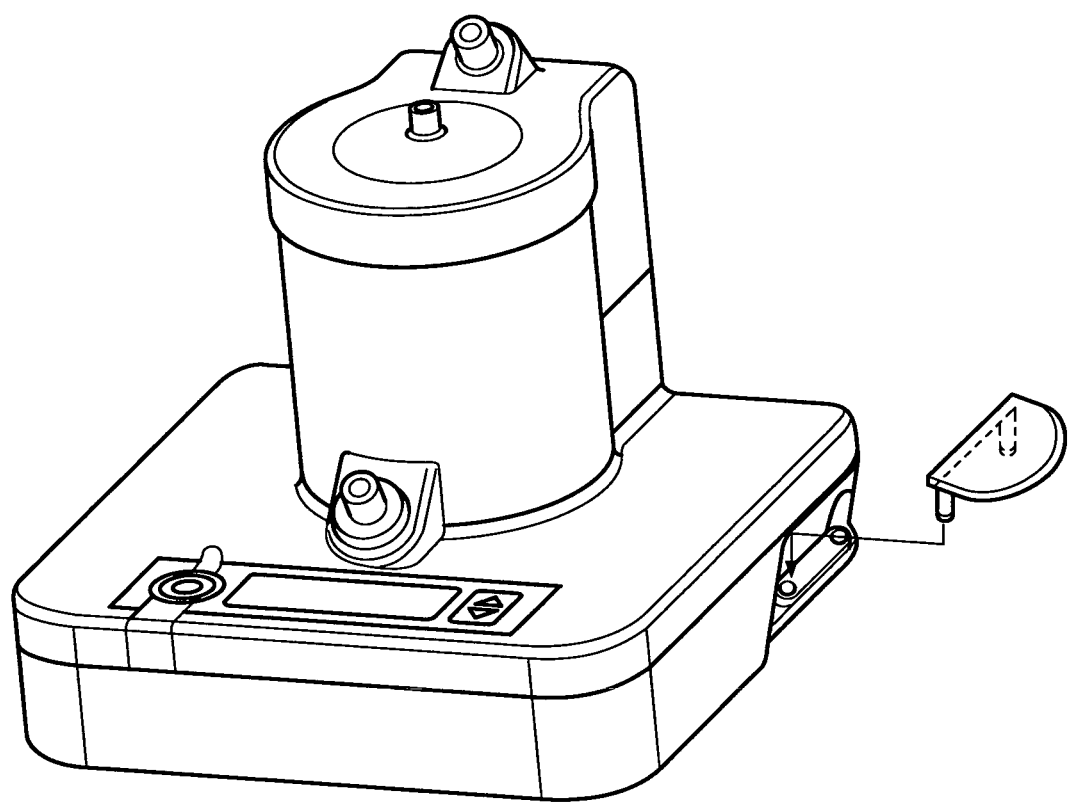
FIG. 19: A schematic view of an alternative embodiment of the apparatus incorporating a mechanical tilt mechanism.
Figure 20:
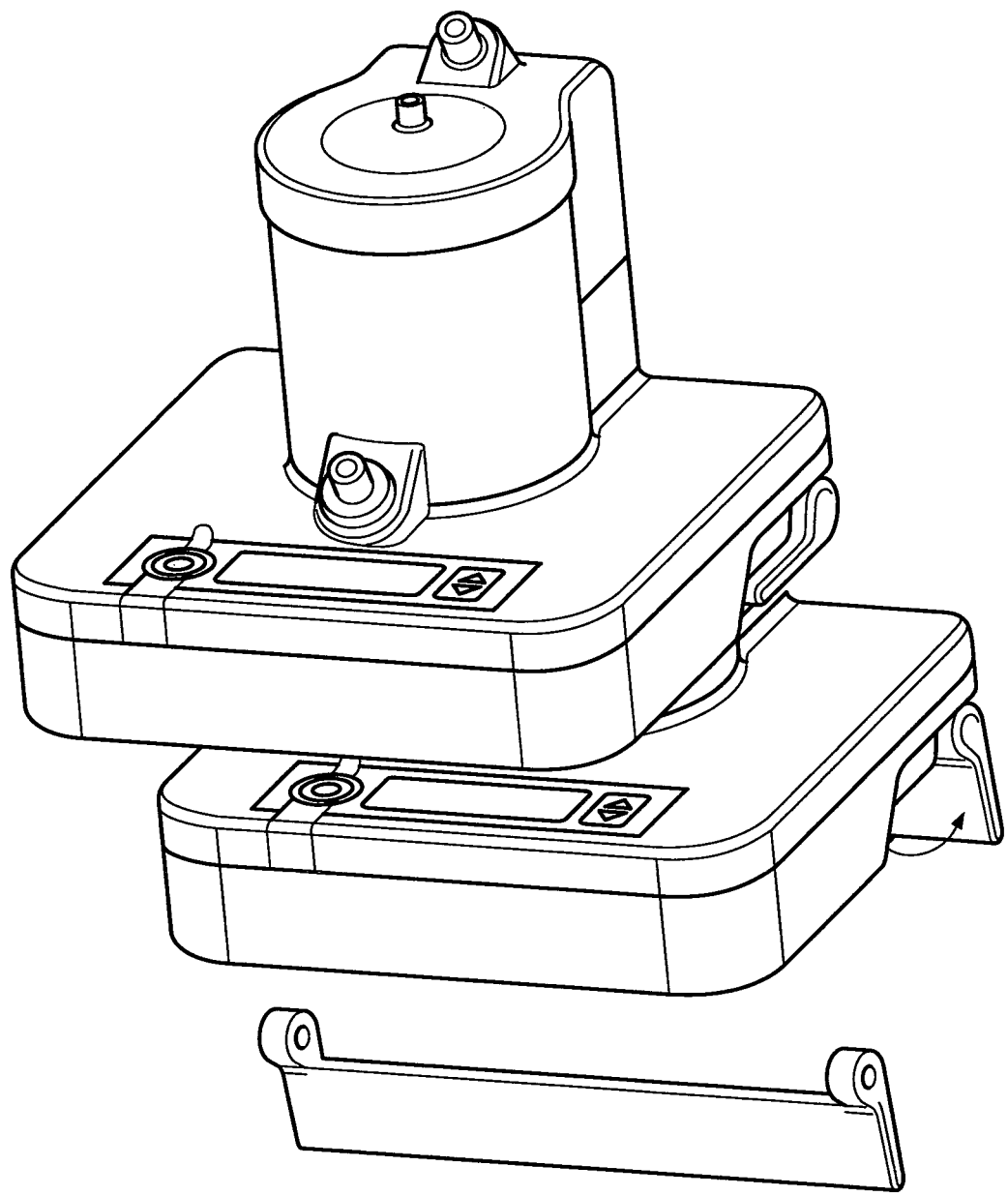
FIG. 20: A schematic view of an embodiment of the apparatus incorporating a mechanical tilt mechanism.
Figure 21:
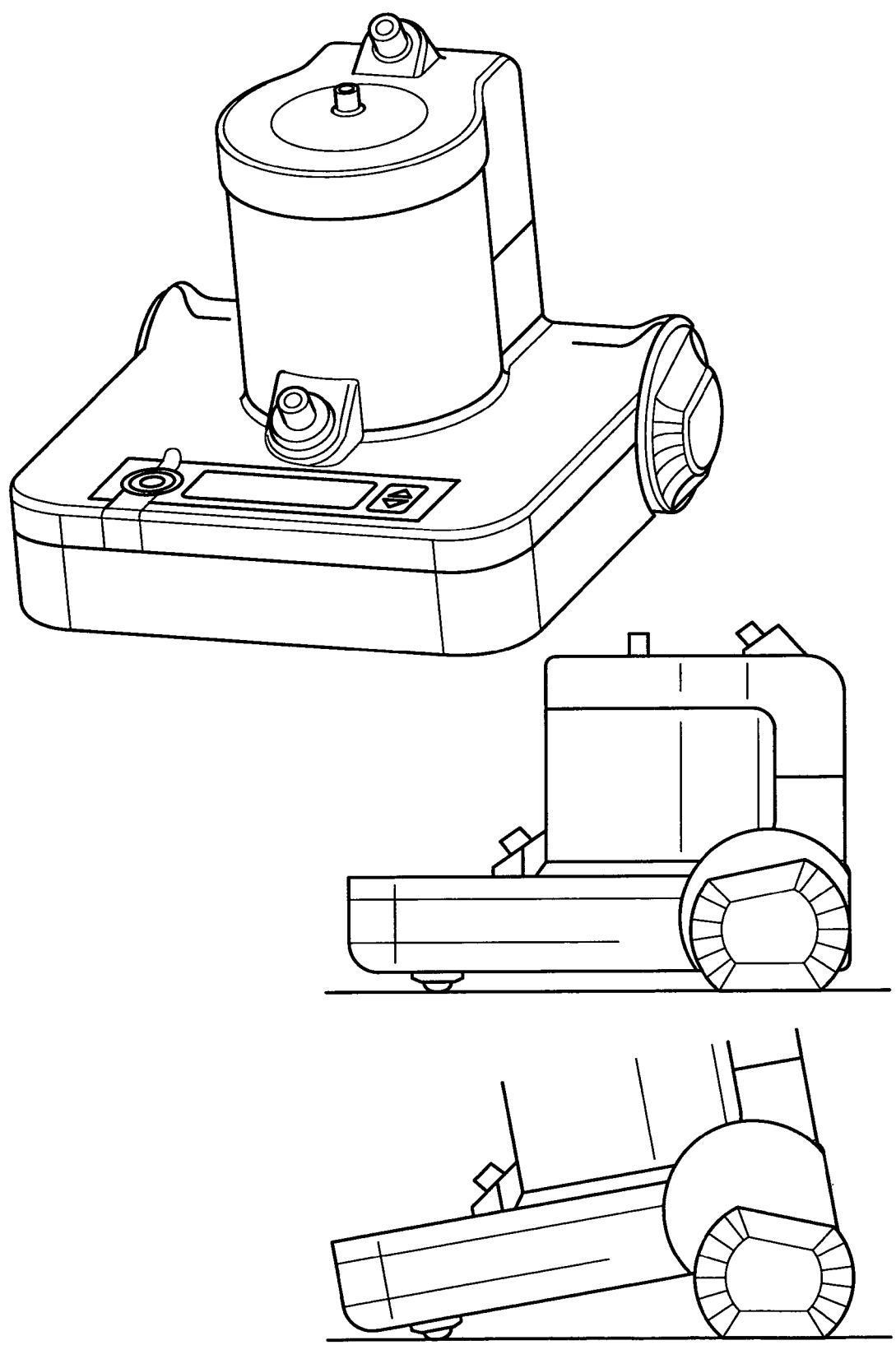
FIG. 21: A schematic view of an alternative embodiment of the apparatus incorporating a mechanical tilt mechanism.
Figure 22:
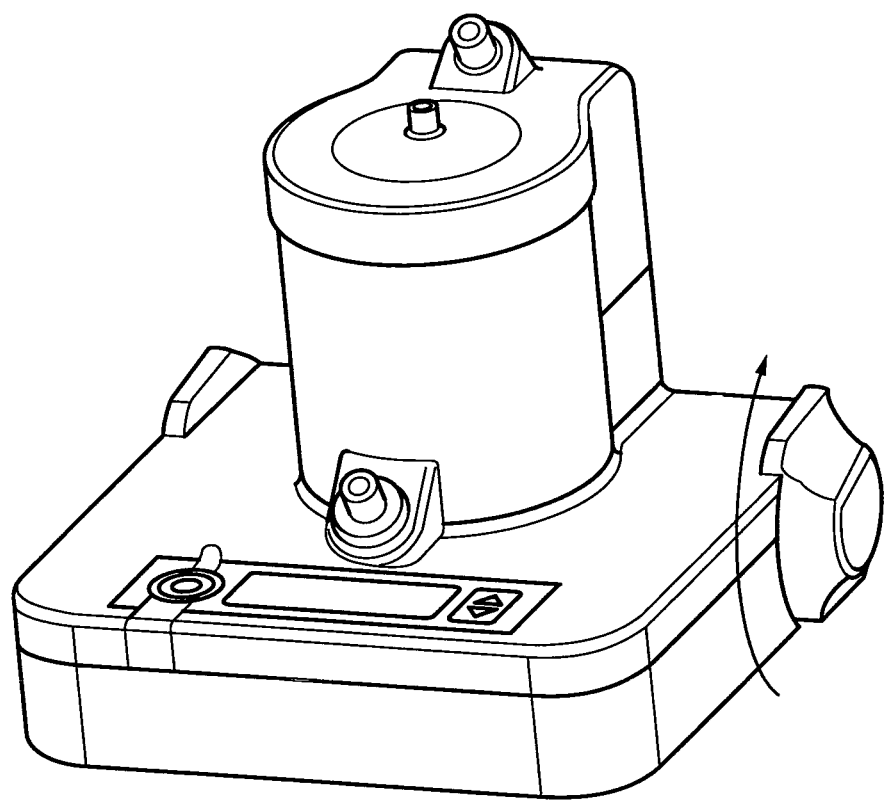
FIG. 22: A schematic view of an alternative embodiment of the apparatus incorporating a mechanical tilt mechanism.
Figure 23:
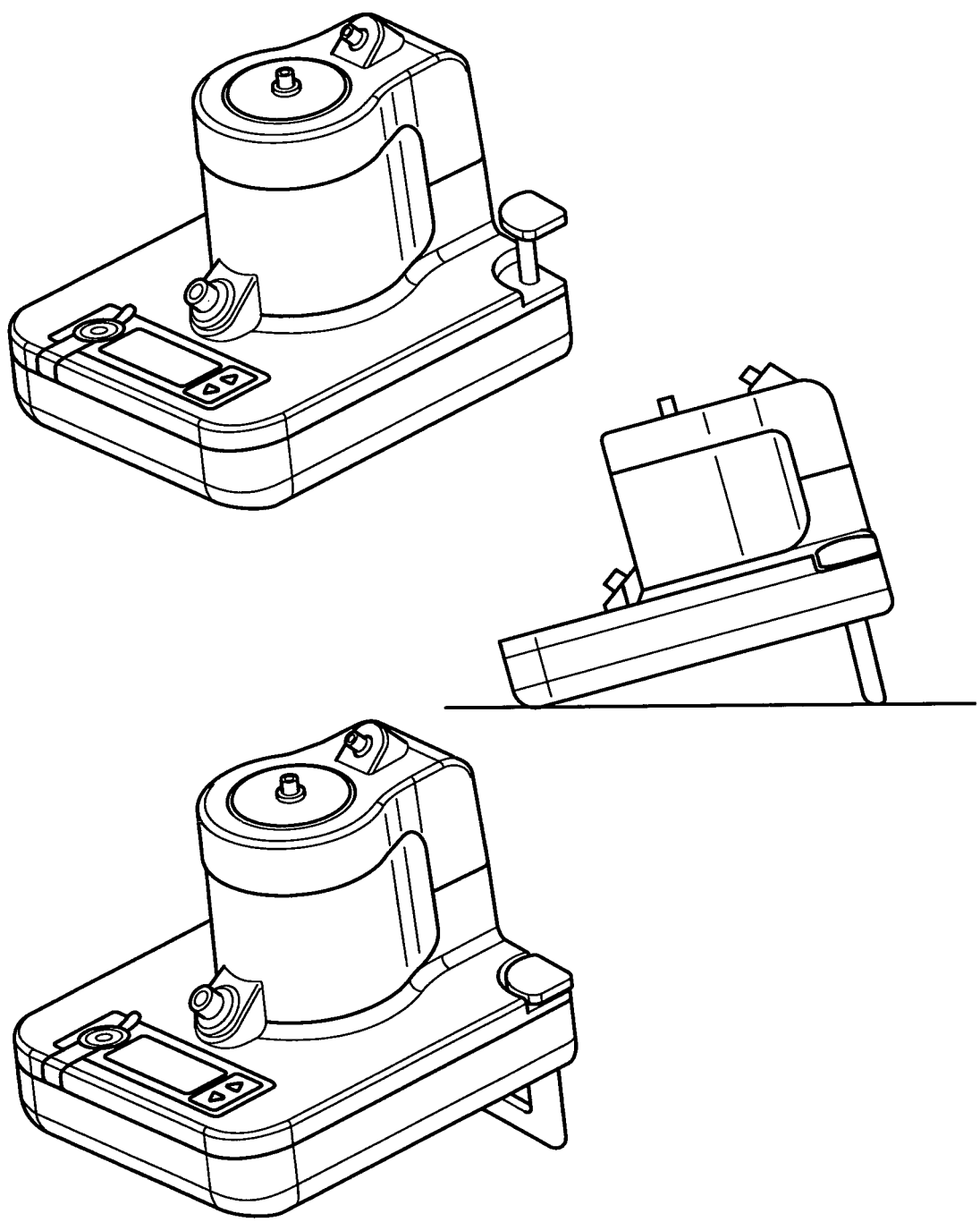
FIG. 23: A schematic view of an alternative embodiment of the apparatus incorporating a mechanical tilt mechanism.
Figure 24:
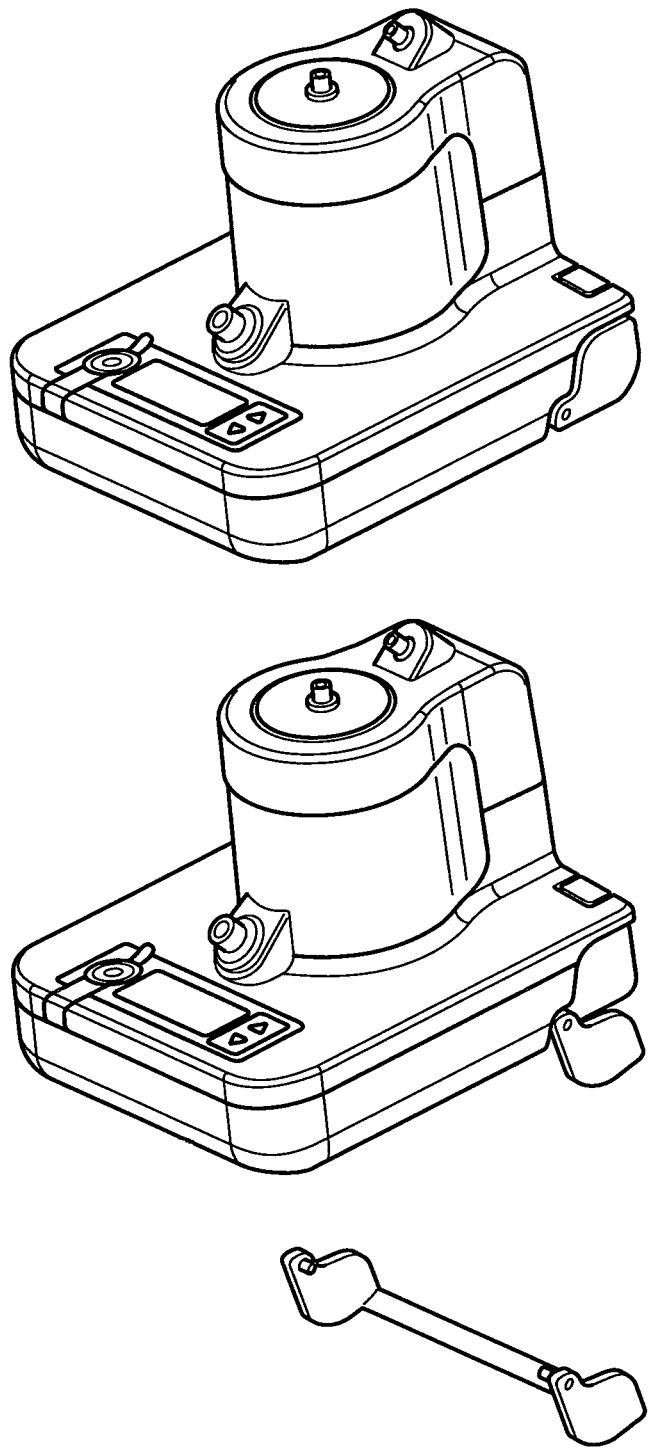
FIG. 24: A schematic view of an alternative embodiment of the apparatus incorporating a mechanical tilt mechanism.
Figure 25:
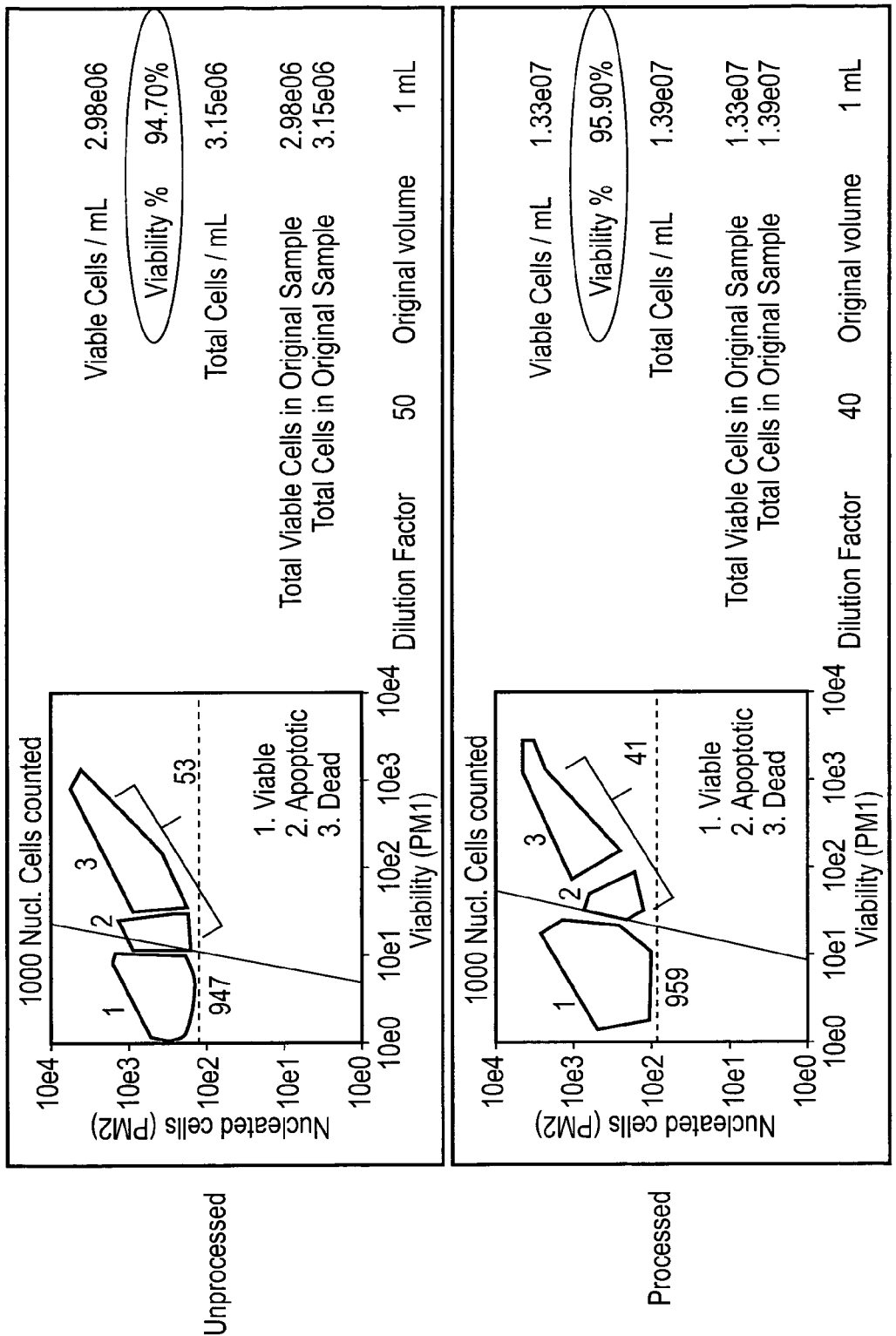
FIG. 25: Cell viability comparison between unprocessed and unprocessed human BMA using the apparatus of the invention.
Figure 26:
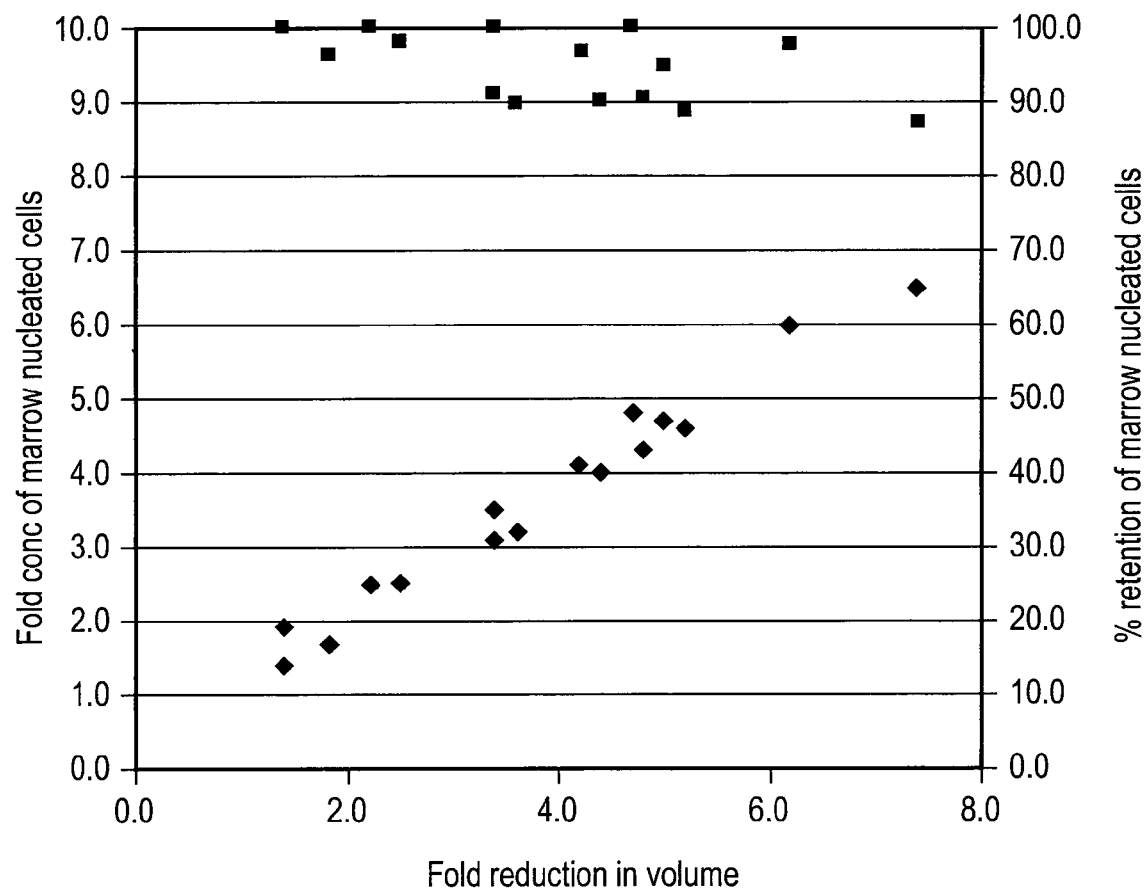
FIG. 26: Retention of TNC and equivalent fold-concentration as a consequence of filtration in the apparatus of the invention.
Figure 27:
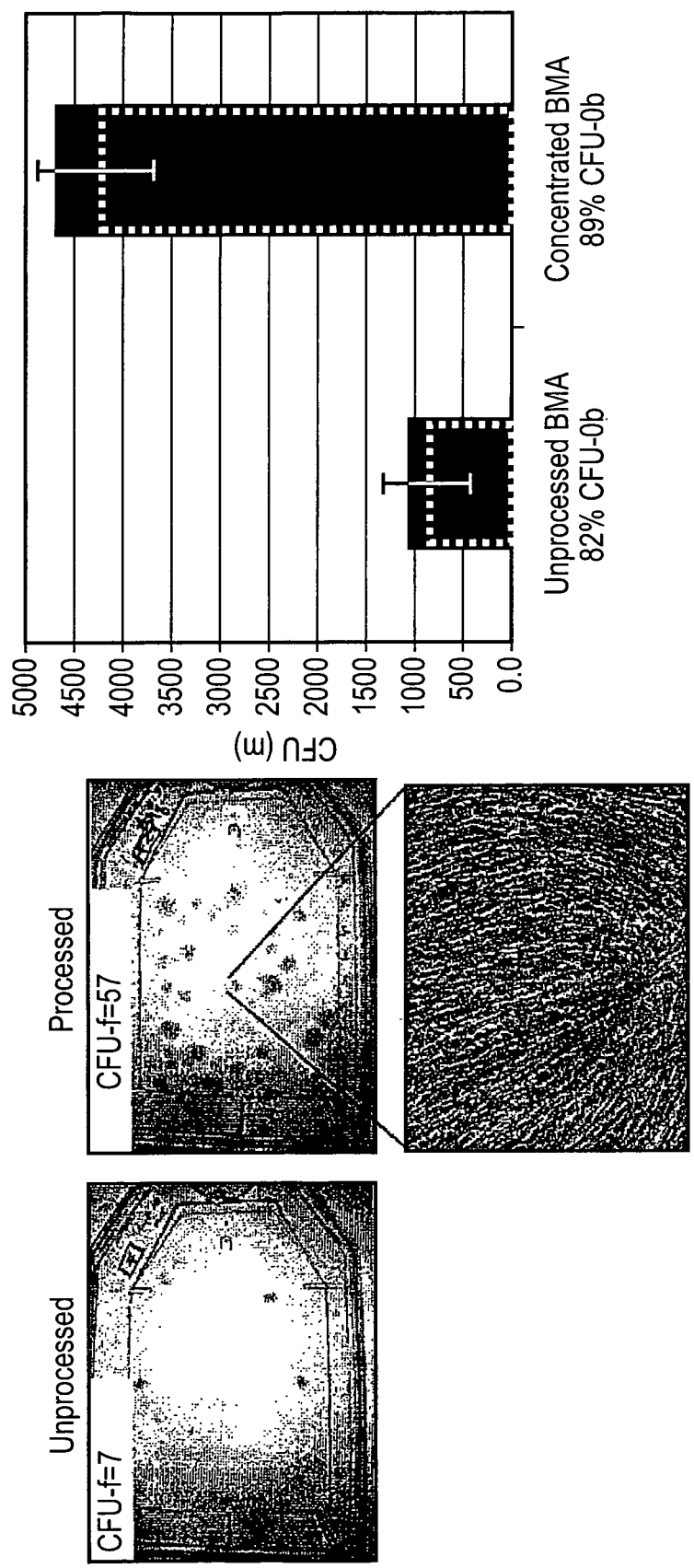
FIG. 27: CFU-f and CFU-Ob comparison between processed and unprocessed BMA for a 9-fold volume reduction. From 25 human BMA samples mean CFU-f was 880/cc for unprocessed samples and 4190/cc for processed samples. Of these, 82% were CFU-Ob and 89% CFU-Ob for unprocessed and processed respectively.
Figure 28:
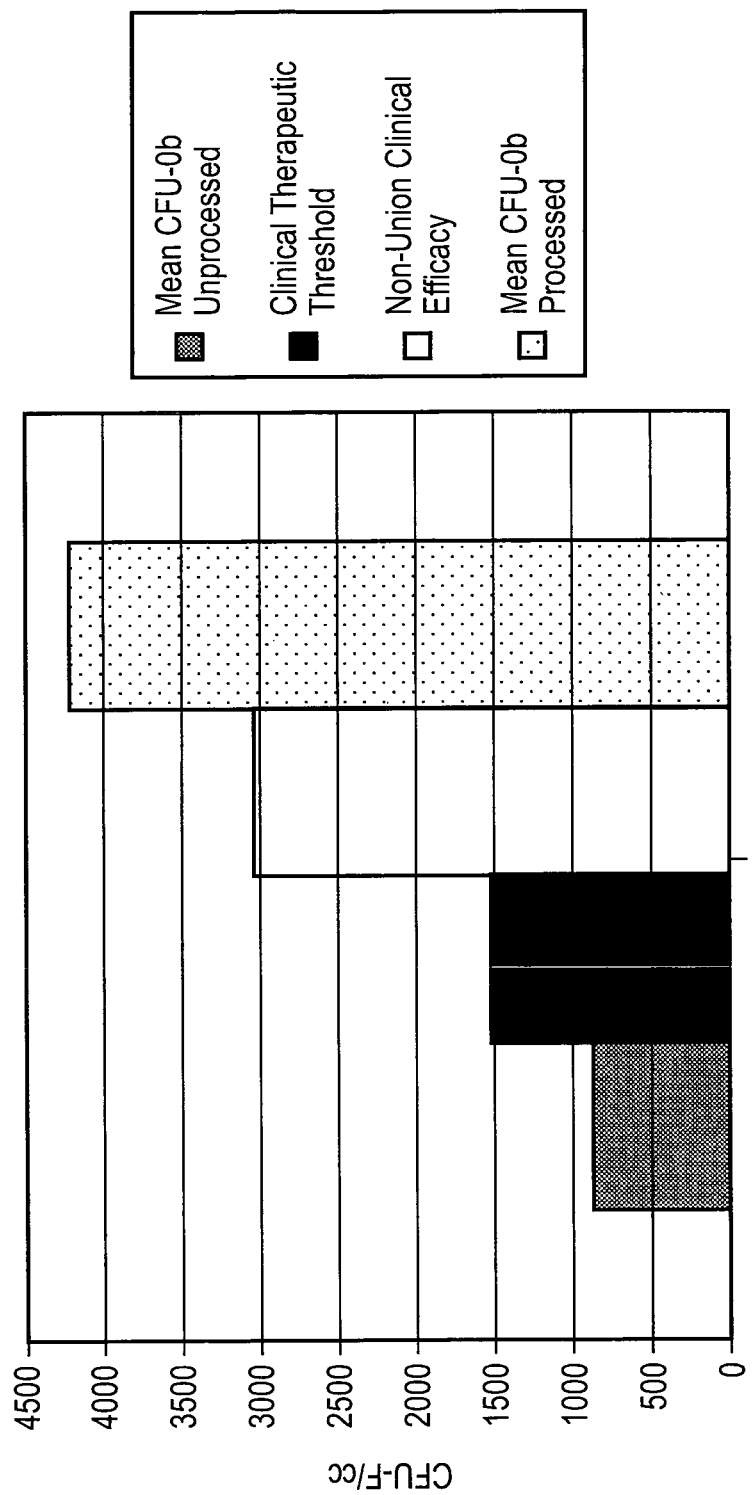
FIG. 28: . Clinical efficacy of concentrated BMA from apparatus of the invention based on a non-unionfracture study by Hernigou

In FIG. 17, a tilt lever 81 is hingedly mounted to the base 82 of a separation device. The tilt lever 81 comprises a span portion 82 and a pair of arms 83 with hinge pins 84. The hinge pins of the arms are adapted for snap fitting into complementary hinge recesses (not shown) in the base. As illustrated, when fitted to the base, the tilt lever 81 can be moved by hand from a first position (step 1) in which it is substantially recessed in the base, to a second position (step 4) in which the span portion projects from a bottom of the base causing the device to assume a tilted orientation on a surface on which it is disposed.

A pair of recesses (not shown) are provided in opposed side walls of the base to enable the tilt lever 81 to be accessed easily by a user's fingers. The resulting tilt angle is determined by the width and angle of the span portion 82 when in the second position.

The invention claimed is:

1. An apparatus for separating a solid fraction from a fluid sample, the apparatus comprising:
a filtration unit comprising:
an energy generating element;
at least one filter which divides the unit into a pre-filtration chamber for receiving the fluid sample and a post-filtration chamber for receiving a fluid; and
a substrate configured to be associated with the fluid in the post-filtration chamber and with the energy generating element such that the energy generating element is operable to transmit energy through the substrate which in turn transmits energy through the fluid in the post-filtration chamber and through the fluid sample within the pre-filtration chamber;
a sensor capable of measuring an amount of fluid in the pre-filtration chamber;
a controller capable of controlling characteristics of energy made by the energy generating element as a function of the measured amount of fluid in the pre-filtration chamber; and a suction device to remove fluid from the post-filtration chamber, thereby applying a vacuum pressure across the filter so as to generate a net unidirectional flow of fluids through the filter from the pre-filtration chamber to the post-filtration chamber.

2. The apparatus of claim 1, wherein the energy generating element is capable of generating vibrational and/or acoustical energy.

3. The apparatus of claim 2, further comprising a pressure sensor to measure the vacuum pressure, wherein the pressure sensor is linked to the controller, and the controller to the suction device to provide feedback-based control of the vacuum pressure.

4. The apparatus of claim 3, further comprising a monitor for measuring energy delivered to one or both fluids.

5. The apparatus of claim 4, wherein the energy measured for is acoustic energy and the monitor is a microphone or other acoustic sensing device.

6. The apparatus of claim 4, wherein the monitor is linked to the controller, and the controller to the energy generating element, thereby to provide feedback-based control of the energy within one or both fluids in the apparatus.

7. The apparatus of claim 2, wherein the sensor measures an amount by volume in the pre-filtration chamber.

8. The apparatus of claim 2, wherein the sensor measures an amount by weight in the pre-filtration chamber.

9. The apparatus of claim 8, wherein changes in fluid volume, pressure, or energy are registered by the microprocessor which adjusts the energy generating element and the suction device to deliver preferred levels of energy and pressure to process the fluids through the separation device.

10. The apparatus of claim 8, wherein the controller is configured to terminate the separation process upon detection of predetermined events, such as the filter being blocked or clogged, the volume of pre-filtration fluid reaching zero, and/ or an unexpected loss of vacuum pressure.

11. An apparatus for separating a solid fraction from a fluid sample, the apparatus comprising:
a filtration unit comprising:
an energy generating element;
at least one filter which divides the unit into a pre-filtration chamber for receiving the fluid sample and a post-filtration chamber for receiving a fluid filtrate thereof; and
a substrate configured to be associated with the post-filtration chamber and to be associated with the energy generating element, such that the energy generating element is operable to transmit energy to the substrate, which in turn transmits energy through both the fluid within the post-filtration chamber and the fluid sample within the pre-filtration chamber;
a sensor to measure an amount of fluid in the pre-filtration chamber; a controller to control at least the energy generating element so as to adjust characteristics of the energy produced as a function of the measured amount of fluid in the pre-filtration chamber; and
a device to apply a first pressure to move fluid from the post-filtration chamber through the filter into the pre-filtration chamber, and a device to apply a second pressure to move fluid from the pre-filtration chamber though the filter to the post-filtration chamber.

12. A system for separating a solid fraction from a fluid sample, the system comprising:
a filtration unit comprising:
an energy generating element;
at least one filter which divides the unit into a pre-filtration chamber for receiving the fluid sample and a post-filtration chamber for receiving a fluid filtrate from the at least one filter and the pre-filtration chamber; and
a substrate configured to be associated with the post-filtration chamber and with the energy generating element such that energy made by the energy generating element is operable to transmit energy to the substrate which in turn transmits energy to both the fluid within the post-filtration chamber and the fluid sample within the pre-filtration chamber;
a sensor to measure an amount of fluid in the pre-filtration chamber;
a controller to control at least the energy generating element so as to adjust characteristics of the energy produced as a function of the measured amount of fluid in the pre-filtration chamber; and
a filter tipping device to tilt at least the pre-filtration chamber so as to facilitate collection of the material within the pre-filtration chamber.

13. The system of claim 12, further comprising: an electronic measuring device to measure a degree of filtration and for generating a signal when a predetermined degree of filtration has been achieved; wherein the filter tilting device is operable to tilt the filter in response to the signal from the electronic measuring device.

14. A system for separating a solid fraction from a fluid sample, the system comprising:
a filtration unit comprising:
an energy generating element;
at least one filter which divides the unit into a pre-filtration chamber for receiving the fluid sample and a post-filtration chamber for receiving a fluid filtrate from the pre-filtration channel and at least one filter; and
a substrate configured to be associated with the post-filtration chamber and with the energy generating element, the substrate when associated with the energy generating element capable of at least one of motion, vibration, resonation, or movement in response to the energy generating element which in turn transmits energy through both the fluid within the post-filtration chamber and the fluid sample within the pre-filtration chamber;

an amount sensor to measure an amount of fluid in the pre-filtration chamber;

a controller to control at least the energy generating element so as to adjust characteristics of the energy generated as a function of the measured amount of fluid in the pre-filtration chamber;

an electronic measuring device to measure a degree of filtration and for generating a signal when a predetermined degree of filtration has been achieved; and a filter tilting device to tilt the filter from a first orientation relative to a horizontal plane to a second orientation relative to the horizontal plane; wherein the filter tilting device is operable to tilt the filter in response to the signal from the electronic measuring device.

* * * * *